US 6,535,278 B1

(12) United States Patent
Imura

(10) Patent No.: US 6,535,278 B1
(45) Date of Patent: Mar. 18, 2003

(54) APPARATUS AND METHOD FOR MEASURING SPECTRAL PROPERTY OF FLUORESCENT SAMPLE

(75) Inventor: Kenji Imura, Toyohashi (JP)

(73) Assignee: Minolta Co., Ltd., Osaka (JP)

( * ) Notice: Subject to any disclaimer, the term of this patent is extended or adjusted under 35 U.S.C. 154(b) by 0 days.

(21) Appl. No.: 09/500,481

(22) Filed: Feb. 9, 2000

(30) Foreign Application Priority Data

Feb. 9, 1999 (JP) .......................................... 11-031815

(51) Int. Cl.[7] .................................................. G01J 3/00
(52) U.S. Cl. ...................... 356/73; 356/319; 250/461.1
(58) Field of Search ........................... 356/72, 73, 319, 356/323, 325, 326, 328, 317, 318; 250/461.1

(56) References Cited

U.S. PATENT DOCUMENTS 5,636,015 A 6/1997 Imura et al. .................. 356/72

Primary Examiner—F. L. Evans
(74) Attorney, Agent, or Firm—McDermott, Will & Emery

(57) ABSTRACT

In an apparatus for measuring a spectral property such as a total spectral radiant factor of a fluorescent sample, a weight factor is previously calculated by using a standard fluorescent sample in which an index of a spectral property such as a total spectral radiant factor is known. When a spectral intensity distribution of a fluorescent sample to be measured is measured, the measured spectral intensity distribution is corrected similar to a value when the fluorescent sample is illuminated as if the same illumination light when the weight factor is set. As a result, the error component in the measurement result due to the variation of the illumination light in a time period from the setting of the weight factor to the measurement of the fluorescent sample can be reduced.

15 Claims, 9 Drawing Sheets

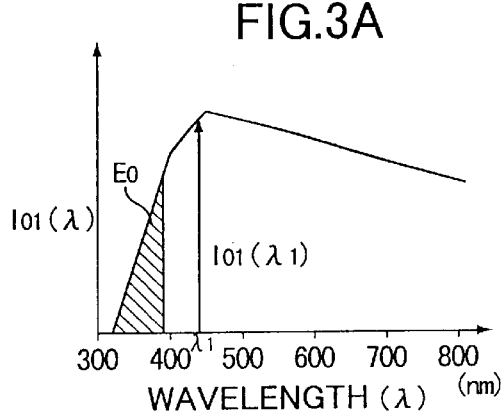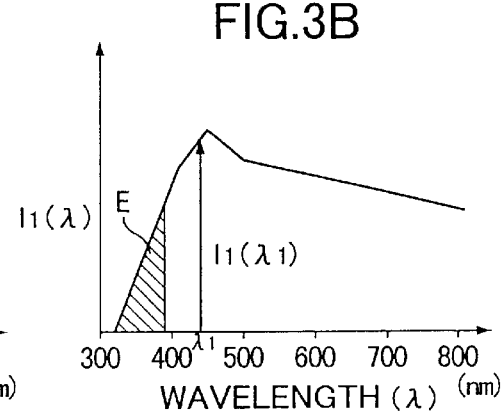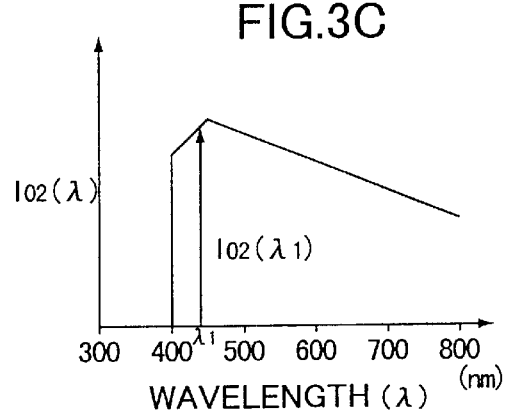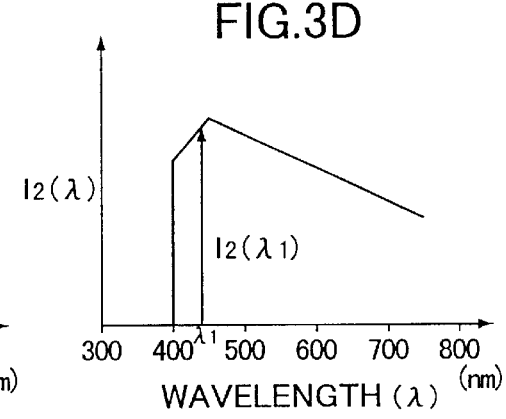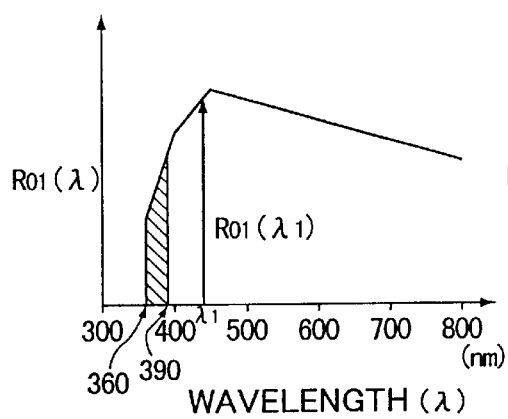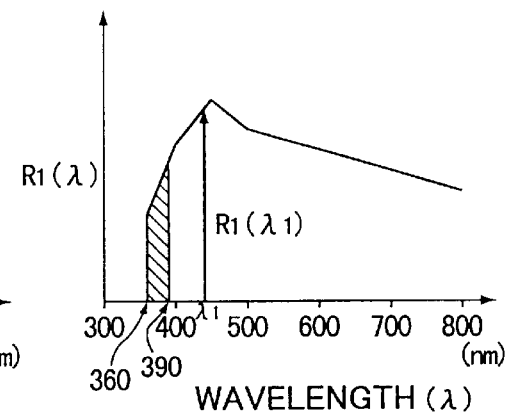

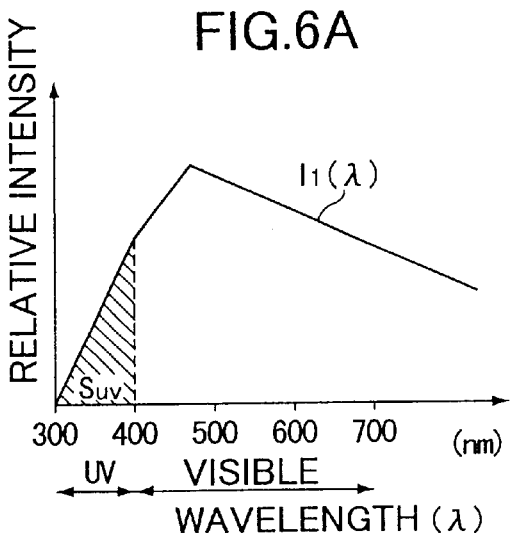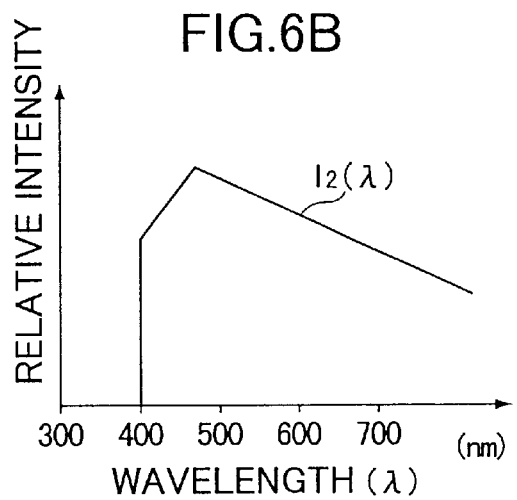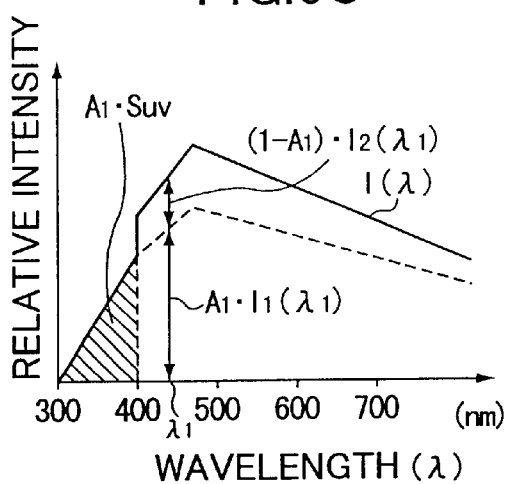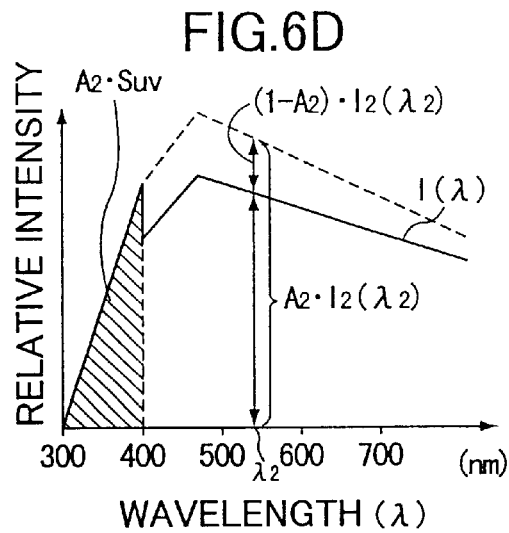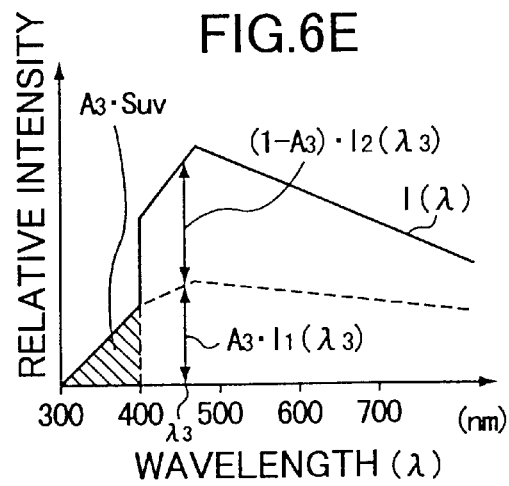

APPARATUS AND METHOD FOR MEASURING SPECTRAL PROPERTY OF FLUORESCENT SAMPLE

This application is based on patent application Hei.11-31815 filed in Japan, the content of which are hereby incorporated by references.

BACKGROUND OF THE INVENTION

1. Field of the Invention

This invention relates to an apparatus and a method for measuring a spectral property of a fluorescent sample including a fluorescent material.

2. Description of the Related Art

Generally, a visual property of a fluorescent sample including a fluorescent material is shown by a total spectral radiant factor. The total spectral radiant factor is a ratio by each wavelength of an emitted light from a sample which is illuminated under a predetermined condition against an emitted light from a perfect reflection diffuser illuminated under the same condition. The total spectral radiant factor $Bt(\lambda)$ is shown by the following equation (1).

$$Bt(\lambda) = Br(\lambda) + Bf(\lambda) \qquad (1)$$

Hereupon, $Br(\lambda)$ is a reflecting spectral radiant factor owing to a reflected light component from the fluorescent sample and $Bf(\lambda)$ is a fluorescent spectral radiant factor owing to a fluorescent light component from the fluorescent sample.

A fluorescent sample having a spectral excitation effect $F(\mu, \lambda)$ is generally excited by a light having a wavelength $\mu$ in ultraviolet (hereinafter abbreviated as UV) region included in the illumination. Thus, the fluorescent spectral radiant factor $Bf(\lambda)$ is shown by the following equation (2).

$$Bf(\lambda) = \int_{UV} I(\mu) \cdot F(\mu,\lambda) d\mu / L(\lambda) \qquad (2)$$

Hereupon, $I(\lambda)$ is a spectral intensity distribution of an illumination light and $L(\lambda)$ is a spectral intensity distribution of a standardized illumination light. As can be shown by the above-mentioned equation, the fluorescent spectral radiant factor $Bf(\lambda)$ depends on the spectral intensity distribution of the illumination light.

When a standard non-fluorescent white sample, in which a reflection spectral radiant factor $Br_w(\lambda)$ thereof is known, is measured by a calorimeter, spectral intensities of the emitted light from the standard sample and the reference light are respectively designated by $S_w(\lambda)$ and $R_w(\lambda)$. When a fluorescent sample is measured by the calorimeter, spectral intensities of the emitted light from the fluorescent sample and the reference light are respectively designated by $S(\lambda)$ and $R(\lambda)$. The total spectral radiant factor $Bt(\lambda)$ of the fluorescent sample is shown by the following equation (3).

$$Bt(\lambda) = Br_w(\lambda) \cdot \{(S(\lambda)/R(\lambda))/\{S_w(\lambda)/R_w(\lambda)\} \qquad (3)$$

As mentioned above, the total spectral radiant factor of the fluorescent sample depends on the spectral intensity of the illumination light, so that it is necessary to coincide the spectral intensity distribution of the illumination light with the spectral intensity distribution of an assumed illumination light used for the measurement.

As an illumination light, a standard D65 illuminant (day light) and a standard A illuminant (incandescent lamp) are well known. Furthermore, D50, D55 and D75 illuminants (day light) and F1, F3 and F11 illuminants (fluorescent lamp) are known. Spectral intensity distribution of these illuminants are defined by CIE (Commission Internationale de l'Eclairage).

In the estimation of the fluorescent sample, it is preferable to use the standard D65 illuminant as an illumination light. It, however, is difficult to obtain an artificial illuminant similar to the standard D65 illuminant. Thus, a relative UV intensity of an illuminant, which is a ratio of the intensity of the illuminant in the UV region against that of the visible region, is calibrated by Gaetner-Griesser method (See "Assessment of Whiteness and Tint of Fluorescent Substrates with Good Instrument Correlation" Rolf Griesser, "The Calibration of Instruments for the Measurement of Paper Whiteness" Anthony Bristow/COLOR Research and Application Vol.19 No.6 December 1994).

Details of the calibration of the relative UV intensity of the illuminant is described with reference to FIG. 9. As can be seen from FIG. 9, a fluorescent sample 1 is disposed at a sample aperture 21 for sample of an integration sphere 2. A lamp 101 such as a xenon lamp having a sufficient UV intensity is driven by an emitting circuit 104. A light flux 102 emitted from the lamp 101 enters into the integration sphere 2 through a light source aperture 23. A UV cutoff filter 103 is provided in a manner to cut the light flux 102 partially. A component of UV is removed from the light flux 102 passing through the UV cutoff filter 103. Thus, the relative UV intensity of an illumination light can be calibrated by adjusting the position (insertion ratio) of the UV cutoff filter 103.

The light flux 102 in the integration sphere 2 is diffusely reflected by an inner surface of the integration sphere 2, and diffusely illuminates the fluorescent sample 1. A radiant light 11 radiated from the fluorescent sample 1 passes through an observation aperture 24 and enters into a first spectroscope 105 used for measuring a spectral intensity distribution $S(\lambda)$ of the fluorescent sample 1. A reference light 62 having substantially the same spectral intensity distribution of the illumination light enters into an optical fiber 61 by which the reference light 62 is guided to a second spectroscope 106. Thus, the spectral intensity distribution $R(\lambda)$ of the reference light 62 is measured by the second spectroscope 106.

For calibrating the relative UV intensity, a non-fluorescent white standard sample 12, in which the reflection spectral radiant factor $Br_w(\lambda)$ thereof is known, is disposed at the sample aperture 21. A spectral intensity distribution $S_w(\lambda)$ of a radiant light from the fluorescent white standard sample 12 and a spectral intensity distribution $R_w(\lambda)$ of the reference light are measured. Subsequently, a standard fluorescent sample 13, in which one of perceived color value such as a CIE whiteness thereof is known, is disposed at the sample aperture 21. A spectral intensity distribution $S(\lambda)$ of a radiant light from the standard fluorescent sample 13 and a spectral intensity distribution $R(\lambda)$ of the reference light are measured. After that, a total spectral radiant factor $Bt(\lambda)$ of the standard fluorescent sample 13 is calculated by the above-mentioned equation (3). When the value of the CIE whiteness obtained by using the total spectral radiant factor $Bt(\lambda)$ of the standard fluorescent sample 13 is not coincide with the known value of the CIE whiteness of the standard fluorescent sample 13, the position of the UV cutoff filter 103 is adjusted until the calculated a value of the CIE whiteness of the standard fluorescent sample 13 coincides with the known value. In this case, the above-mentioned equation (2) is modified to the following equation (4). Hereupon, the symbol "p" designates an attenuation factor in the UV region.

$$Bf(\lambda) = \int_{UV} p \cdot I(\mu) \cdot E(\mu,\lambda) d\mu / L(\lambda) \qquad (4)$$

As mentioned above, the Gaetner-Griesser method needs to move the UV cutoff filter 103, so that the configuration of the apparatus is mechanically complex. Furthermore, it is necessary to repeat the movement of the UV cutoff filter 103 and the measurement of the samples 12 and 13 for calibrating the relative UV intensity, so that time will be wasted for the calibration.

For solving the disadvantage of the Gaetner-Griesser method, an apparatus shown in FIG. 10 is proposed (See U.S. Pat. No. 5,636,015). As can be seen from FIG. 10, a first illumination unit 111 and a second illumination unit 121 are provided. A first light flux 113 including a UV component is emitted from a lamp 112 of the first illumination unit 111 and enters into the integration sphere 2 through a first illuminant aperture 22. A light flux including a UV component is emitted from a lamp 122 of the first illumination unit 121 and a UV component is removed therefrom by a UV cutoff filter 123. A second light flux 124 without including the UV component and passing through the UV cutoff filter 123 enters into the integration sphere 2 through a second illuminant aperture 23.

A standard non-fluorescent white sample 12, in which a spectral reflectance $W(\lambda)$ is known, is disposed at the sample aperture 21. The lamp 112 of the first illumination unit 111 is lit for measuring a spectral intensity distribution $S_{w1}(\lambda)$ of a radiant light 11 from the standard non-fluorescent white sample 12 and a spectral intensity distribution $R_{w1}(\lambda)$ of a reference light 62. The spectral intensity distributions $S_{w1}(\lambda)$ and $R_{w1}(\lambda)$ are memorized in a memory 108. Subsequently, the lamp 122 of the second illumination unit 121 is lit for measuring a spectral intensity distribution $S_{w2}(\lambda)$ of the radiant light 11 from the standard non-fluorescent white sample 12 and a spectral intensity distribution $R_{w2}(\lambda)$ of the reference light 62. The spectral intensity distributions $S_{w2}(\lambda)$ and $R_{w2}(\lambda)$ are memorized in the memory 108.

Similarly, a standard fluorescent sample 13, in which a total spectral radiant factor $Bt_S(\lambda)$ illuminated by a standard D65 illuminant is known, is disposed at the sample aperture 21. The lamp 112 of the first illumination unit 111 is lit for measuring a spectral intensity distribution $S_1(\lambda)$ of a radiant light 11 from the standard fluorescent sample 13 and a spectral intensity distribution $R_1(\lambda)$ of a reference light 62. The spectral intensity distributions $S_1(\lambda)$ and $R_1(\lambda)$ are memorized in the memory 108. Subsequently, the lamp 122 of the second illumination unit 121 is lit for measuring a spectral intensity distribution $S_2(\lambda)$ of the radiant light 11 from the standard fluorescent sample 13 and a spectral intensity distribution $R_2(\lambda)$ of the reference light 62. The spectral intensity distributions $S_2(\lambda)$ and $R_2(\lambda)$ are memorized in the memory 108.

When all the spectral intensity distributions $S_{w1}(\lambda)$, $R_{w1}(\lambda)$, $S_{w2}(\lambda)$, $R_{w2}(\lambda)$, $S_1(\lambda)$, $R_1(\lambda)$, $S_2(\lambda)$ and $R_2(\lambda)$ are measured, a total spectral radiant factor $Bt(\lambda)$ of the standard fluorescent sample 13 is calculated by the following equations (5). Hereupon, symbols $a_1(\lambda)$ and $a_2(\lambda)$ respectively designate weight factor.

$$Bt(\lambda)=W(\lambda)\cdot\{S'(\lambda)/R'(\lambda)\}/\{S_w'(\lambda)/R_w'(\lambda)\}$$

$$S'(\lambda)=a_1(\lambda)\cdot S_1(\lambda)+a_2(\lambda)\cdot S_2(\lambda)$$

$$R'(\lambda)=a_1(\lambda)\cdot R_1(\lambda)+a_2(\lambda)\cdot R_2(\lambda)$$

$$S_w'(\lambda)=a_1(\lambda)\cdot S_{w1}(\lambda)+a_2(\lambda)\cdot S_{w2}(\lambda)$$

$$R_w'(\lambda)=a_1(\lambda)\cdot R_{w1}(\lambda)+a_2(\lambda)\cdot R_{w2}(\lambda)$$

$$a_1(\lambda)+a_2(\lambda)=1 \qquad (5)$$

When the calculated total spectral radiant factor $Bt(\lambda)$ of the standard fluorescent sample 13 does not coincide with the known total spectral radiant factor $Bt(\lambda)$ thereof, the weight factors $a_1(\lambda)$ and $a_2(\lambda)$ are calculated with respect to each wavelength so as to coincide the calculated value with the known value. Consequently, the relative UV intensity is calibrated.

When the weight factors $a_1(\lambda)$ and $a_2(\lambda)$ are calculated, a fluorescent sample 1 which is to be measured is disposed at the sample aperture 21, and the spectral intensity distributions $S_1(\lambda)$, $R_1(\lambda)$, $S_2(\lambda)$ and $R_2(\lambda)$ of the fluorescent sample 1 are measured. After that, the total spectral radiant factor $Bt(\lambda)$ of the fluorescent sample 1 is calculated by following the above-mentioned equation (5).

The prior arts illustrated in the FIGS. 9 and 10 are premised to satisfy the following three conditions. First, an object to be measured is a fluorescent sample including a fluorescent whitening agent which is exited by a UV component of an illumination light and radiates a fluorescence having a wavelength in visible region. Second, the fluorescent sample to be measured includes the fluorescent whitening agent the same as or similar to that of the standard fluorescent sample used in the calibration of the relative UV intensity. Third, the relative UV intensity of the illuminant (especially the light flux 113 from the first illumination unit 111 in the case shown in FIG. 10) is not varied from the calibration of the relative UV intensity to the measurement of the sample.

The above-mentioned first and second conditions can be satisfied by restricting the object to be measured. It, however, is not realistic to be satisfied the third condition because of the following reasons. There is a phenomenon called "integration sphere effect" that reflected light from the sample and fluorescence from the sample (intensity distribution of the fluorescent whitening agent generally has a peak in the vicinity of the wavelength 450 nm) are included in the illumination light in the integration sphere 2. Furthermore, the UV intensity of the light source will be reduced due to the deterioration of the illuminant with age.

When the relative UV intensity of the light source is varied between the calibration and the measurement of the sample, the fluorescent spectral radiant factor $Bf(\lambda)$ includes error component, as can be seen from the above-mentioned equation (2). Such the error component causes the error of the total spectral radiant factor $Bt(\lambda)$ obtained from the fluorescent spectral radiant factor $Bf(\lambda)$.

The error component caused by the deterioration of the light source can be reduced by shortening a time period of a cycle of the calibration of the relative UV intensity. It, however, is difficult to reduce the error component caused by the integration sphere effect, since this phenomenon depends on the characteristics of the sample.

SUMMARY OF THE INVENTION

An object of this invention is to provide an apparatus and a method for measuring a spectral property of a fluorescent sample including a fluorescent material, in which the variation of the relative UV intensity of the light source due to the deterioration of the light source and the integration sphere effect can be calibrated, and the error component in the measurement result due to the variation of the relative UV intensity can be reduced.

An apparatus for measuring a spectral property of a fluorescent sample including a fluorescent material in accordance with this invention comprises a first and second illumination units, a first and second spectroscopes, a memory, a measurement controller and a first to a third processors.

The first illumination unit emits a first illumination light including a ultraviolet component, and the second illumination unit emits a second illumination light including a component having a wavelength longer than a predetermined cutoff wavelength.

The first spectroscope measures a spectral intensity distribution of a radiant light radiated from a sample disposed at a measurement position when the sample is illuminated by the first or second illumination unit, and the second spectroscope measures a spectral intensity distribution of a reference light which is similar to the illumination light from the first or second illumination unit when the sample is illuminated by the illumination light.

The memory memorizes a weight factor.

The measurement controller alternatively controls the first and second illumination units for illuminating a fluorescent sample to be measured at the measurement position, controls the first spectroscope for measuring alternative of a first measured radiant light spectral intensity distribution of a radiant light radiated from the fluorescent sample corresponding to the illumination light from the first illumination unit and a second measured radiant light spectral intensity distribution of a radiant light radiated from the fluorescent sample corresponding to the illumination light from the second illumination unit, and controls the second spectroscope for measuring alternative of a first measured reference light spectral intensity distribution of a reference light corresponding to the illumination light from the first illumination unit and a second measured reference light spectral intensity distribution of a reference light corresponding to the illumination light from the second illumination unit.

The first processor calculates a first total spectral radiant factor of the fluorescent sample by using the first measured radiant light spectral intensity distribution and the first measured reference light spectral intensity distribution, and a second total spectral radiant factor of the fluorescent sample by using the second measured radiant light spectral intensity distribution and the second measured reference light spectral intensity distribution.

The second processor calculates a first corrected total spectral radiant factor by using a ratio of an intensity in a visible portion of the first standard reference light spectral intensity distribution against an intensity in a ultraviolet portion thereof, and a ratio of an intensity in a visible portion of the first measured reference light spectral intensity distribution against an intensity in a ultraviolet portion thereof.

The third processor calculates a total spectral radiant factor of the fluorescent sample by using the corrected total spectral radiant factor, the second total spectral radiant factor and the weight factor.

By such a configuration, the fluorescent sample to be measured disposed at the measurement position is illuminated by the illumination light from the first illumination unit including the UV component, and the first radiant light spectral intensity distribution and the first reference light spectral intensity distribution are measured by the first and second spectroscopes. Furthermore, the first total spectral radiant factor of the fluorescent sample is calculated from these spectral intensity distributions by the first processor.

Subsequently, the fluorescent sample is illuminated by the second illumination light from the second illumination unit without including the UV component, and the second radiant light spectral intensity distribution and the second reference light spectral intensity distribution are measured by the first and second spectroscopes. Furthermore, the second total spectral radiant factor of the fluorescent sample is calculated from these spectral intensity distributions by the first processor.

The first total spectral radiant factor of the fluorescent sample is corrected to the corrected total spectral radiant factor by the second processor in a manner so that the corrected total spectral radiant factor is similar to the total spectral radiant factor of the fluorescent sample when the fluorescent sample is illuminated by the same illumination light at the setting of the weight factor.

The third processor calculates the total spectral radiant factor of the fluorescent sample as a measurement result by linear combination of the weighted corrected total spectral radiant factor and a weighted second total spectral radiant factor by using the weight factor. As a result, an error component due to the variation of the illumination lights in a time period from the first and second illumination units from the setting of the weight factor to the measurement of the fluorescent sample can be reduced, and the accuracy of the measurement result can be increased.

BRIEF DESCRIPTION OF THE DRAWINGS

FIG. 3A is a graph showing an example of a spectral intensity distribution of a first illumination unit when the weight factor is set in the embodiment;

FIG. 3B is a graph shows an example of a spectral intensity distribution of the first illumination unit when a fluorescent sample is measured;

FIG. 3C is a graph showing an example of a spectral intensity distribution of a second illumination unit when the weight factor A is set.

FIG. 3D is a graph showing an example of a spectral intensity distribution of the second illumination unit when the fluorescent sample is measured;

FIG. 4A is a graph showing an example of a spectral intensity distribution of a reference light 62 similar to that of the first illumination unit when the weight factor is set FIG. 4B is a graph showing an example of a spectral intensity distribution of the reference light 62 when the fluorescent sample is measured;

FIG. 6A is a graph showing a spectral intensity distribution of the first illumination unit;

FIG. 6B is a graph showing a spectral intensity distribution of the second illumination unit;

FIG. 6C is a graph showing a linearly composed spectral intensity distribution of the illumination light when the weight factor $A(\lambda)=A_1<1$;

FIG. 6D is a graph showing a linearly composed spectral intensity distribution of the illumination light when the weight factor $A(\lambda)=A_2>1$;

FIG. 6E is a graph showing a linearly composed spectral intensity distribution of the illumination light when the weight factor $A(\lambda)=A_3<A_1<1$;

DETAILED DESCRIPTION OF THE EMBODIMENT

An embodiment of an apparatus and a method for measuring a spectral property of a fluorescent sample in accordance with this invention is described.

Figure 1:
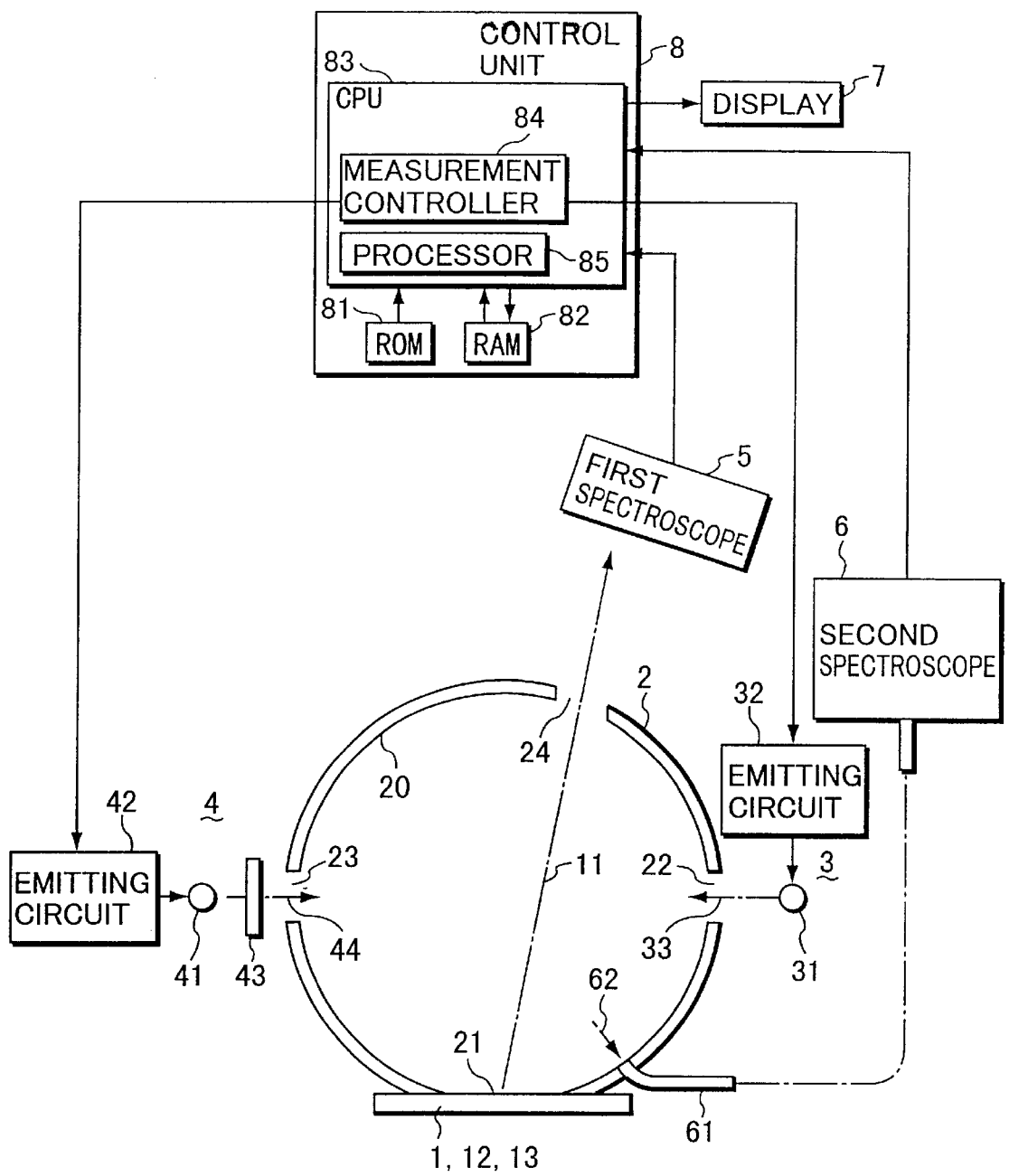
FIG. 1 is a cross-sectional front view showing a configuration of an embodiment of an apparatus for measuring spectral property of a fluorescent sample in accordance with this invention.

FIG. 1 shows a configuration of an apparatus for measuring spectral property of a fluorescent sample in this embodiment. The apparatus is used for obtaining, for example, a total spectral radiant factor of a fluorescent sample 1. The apparatus comprising an integration sphere 2, a first illumination unit 3, a second illumination unit 4, a first spectroscope 5 for the sample, a second spectroscope 6 for reference light, a display 7 and a control unit 8.

The integration sphere 2 is used for generates a diffused illumination light by multiple diffuse reflection of an incident light flux. A white diffusing refraction material such as MgO and $BaSO_4$ is coated on an inner surface 20 of the integration sphere 2. The integration sphere 2 has a sample aperture 21, a first illuminant aperture 22, a second illuminant aperture 23 and an observation aperture 24. A fluorescent sample 1 to be measured is, for example, a cloth or a paper including a fluorescent material. The fluorescent sample 1 is disposed at the sample aperture 21 of the integration sphere 2.

Alternatively, a standard non-fluorescent white sample 12 or a standard fluorescent sample 13 is disposed at the sample aperture 21. The standard non-fluorescent white sample 12, in which a reflection spectral radiant factor $Br_w(\lambda)$ thereof is known, is used for calibrating reflectance factor of the apparatus. The standard fluorescent sample 13, in which a total spectral radiant factor $Bt_s(\lambda)$ thereof illuminated by a predetermined illuminant is known, is used for calibrating a relative UV intensity of the illuminant of the apparatus.

The first illumination unit 3 comprises a first lamp 31 and a first emission circuit 32. The first lamp 31 such as a xenon flash lamp emitting a light flux including a UV component is disposed in the vicinity of the first illuminant aperture 22 of the integration sphere 2. The first emitting circuit 32 drives the first lamp 31 for generating pulsating light flux 33. The light flux 33 including the UV component enters into the integration sphere 2 through the first illuminant aperture 22.

The second illumination unit 4 comprises a second lamp 41, a second emitting circuit 42 and a cutoff filter 43. The second lamp 41 such as a xenon flash lamp emitting a light flux including a UV component is disposed in the vicinity of the second illuminant aperture 23 of the integration sphere 2. The UV cutoff filter 43 is disposed between the second lamp 41 and the second illuminant aperture 23. The UV cutoff filter 43 transmits only a light flux having a wavelength longer than a predetermined cutoff wavelength $\lambda_{C1}$ (for example, $\lambda_{C1}$=400 nm). Thus, the UV light flux having the wavelength shorter than the cutoff wavelength $\lambda_{C1}$ can be removed from the light flux emitted from the second lamp 41 by the UV cutoff filter 43. The second emitting circuit 42 drives the second lamp 41 for generating pulsating light flux. A light flux 44 from which the UV component is removed enters into the integration sphere 2 through the second illuminant aperture 23.

The light fluxes 33 and 44 entering into the integration sphere 2 are multiply reflected diffusely on the inner surface 20 of the integration sphere 2 and diffusely illuminate a sample such as the fluorescent sample 1, the standard non-fluorescent white sample 12 and the standard fluorescent sample 13 disposed at the sample aperture 21 (measurement position). A radiant light 11 radiated in a predetermined direction from the sample 1, 12 or 13 passes through the observation aperture 24 and enters into the first spectroscope 5 used for measuring a spectral property such as a spectral intensity distribution of the radiant light 11. Measurement data obtained by the first spectroscope 5 is transmitted to the control unit 8.

An incident end of an optical fiber 61 is disposed in the vicinity of the sample aperture 21 of the integration sphere 2. An exit end of the optical fiber 61 faces to the second spectroscope 6. A reference light 62 entering into the optical fiber 61 is guided to the second spectroscope 6. Thus, the spectral intensity distribution of the reference light 62 is measured by the second spectroscope 6. Measurement data obtained by the second spectroscope 6 is transmitted to the control unit 8. Since the incident end of the optical fiber 61 is disposed in the vicinity of the sample aperture 21, a spectral intensity distribution of the reference light 62 is substantially the same as that of the illumination light. Consequently, it is substantially equivalent that spectral property of the illumination light is monitored by the second spectroscope 6.

The display 7 is, for example, a CRT (Cathode Ray Tube apparatus) for displaying a calculated result such as a total spectral radiant factor calculated by the control unit 8.

The control unit 8 for controlling the sequence of the apparatus and the contents of the display 7 comprises a ROM 81, a RAM 82 and a CPU 83. The CPU 83 is connected to the first spectroscope 5, the second spectroscope 6, the display 7, the first emitting circuit 32 and the second emitting circuit 42. The CPU 83 functionally serves as a measurement controller 84 and a processor 85.

The ROM 81 memorizes a control program of the CPU 83, the known reflection spectral radiant factor $Br_w(\lambda)$ of the standard non-fluorescent white sample 12, the known total spectral radiant factor $Bt_s(\lambda)$ of the standard fluorescent sample 13, and so on.

The RAM 82 memorizes the measurement data such as a calculated weight factor $A(\lambda)$, spectral intensity distributions of the standard fluorescent sample 13 and the reference light which are to be used for calculating the weight factor $A(\lambda)$, and so on. Details for calculating the weight factor $A(\lambda)$ will be described below.

The measurement controller 84 not only controls the first and second emitting circuits 32 and 42 for lighting the first and second lamps 31 and 41 when a spectral property of the sample 1, 12 or 13 disposed at the sample aperture 21 is measured, but also memorizes the measurement data such as the spectral intensity distribution obtained by the first and second spectroscope 5 and 6 into the RAM 82.

The processor 85 has the following functions. First, the processor 85 serves as a first processor for calculating a first total spectral radiant factor $Bt_1(\lambda)$ when the fluorescent sample 1 is illuminated by a first illumination light from the first illumination unit 3 and a second total spectral radiant factor $Bt_2(\lambda)$ when the fluorescent sample 1 is illuminated by a second illumination light from the second illumination unit 4 from the measurement data such as the spectral intensity distributions obtained by the first and second spectroscopes 5 and 6. Second, the processor 85 has a function for memorizing the calculated result into the RAM 82.

Third, the processor 85 serves as a second processor for calculating a corrected total spectral radiant factor $Bt_{O1}(\lambda)$ which is a corrected value of the first total spectral radiant factor $Bt_1(\lambda)$ by a process described below. Fourth, the processor 85 has a function for memorizing the corrected total spectral radiant factor $Bt_{O1}(\lambda)$ into the RAM 82.

Fifth, the processor 85 serves as a third processor for calculating the weight factor $A(\lambda)$ of the first and second total spectral radiant factors $Bt_1(\lambda)$ and $Bt_2(\lambda)$. Sixth, the processor 85 has a function for memorizing the weight factor $A(\lambda)$ into the RAM 82.

Seventh, the processor 85 serves as a fourth processor for calculating the total spectral radiant factor $Bt(\lambda)$ of the fluorescent sample 1 by linear combination of the corrected total spectral radiant factor $Bt_{O1}(\lambda)$ and the second spectral radiant factor $Bt_2(\lambda)$ by using the weight factor $A(\lambda)$.

It is preferable that the CUP 83 further has a function for calculating an index with respect to a color value, a CIE whiteness, and so on from the calculated total spectral radiant factor $Bt(\lambda)$.

Figure 2:
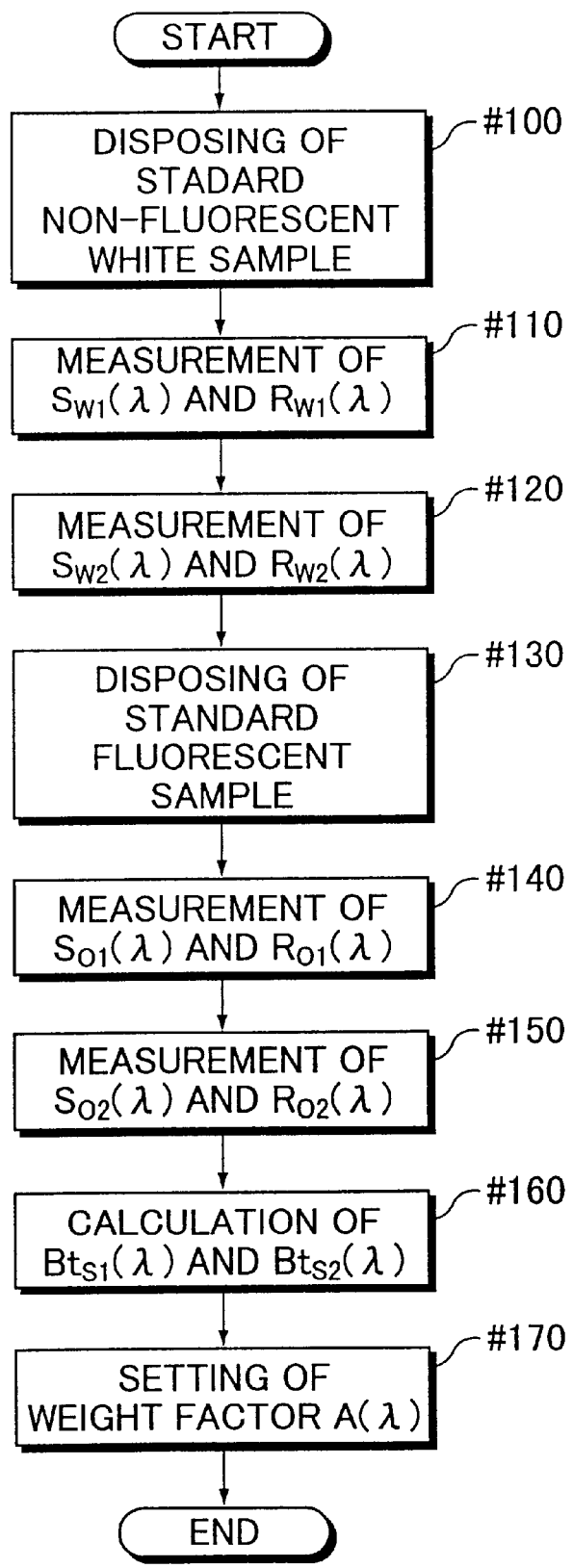
FIG. 2 is a flowchart showing a process for setting a weight factor in the embodiment.

The process for obtaining the weight factor $A(\lambda)$ is described with reference to FIGS. 1 and 2. FIG. 2 is a flowchart showing the process.

At first, calibration of the reflectance factor of the apparatus is executed by using the standard non-fluorescent white sample 12 including no fluorescent material. The standard non-fluorescent white sample 12 is disposed at the sample aperture 21 of the integration sphere 2 (Step #100). As mentioned above, the reflection spectral radiant factor $Br_w(\lambda)$ of the standard non-fluorescent white sample 12 is known. Under this condition, the measurement controller 84 controls the first emitting circuit 32 for lighting the first lamp 31 pulsatively. The spectral intensity distribution $S_{w1}(\lambda)$ of the radiant light 11 from the standard non-fluorescent white sample 12 and the spectral intensity distribution $R_{w1}(\lambda)$ of the reference light 62 are respectively measured by the first and second spectroscopes 5 and 6. The measurement results are memorized in the RAM 82 (Step #110).

Subsequently, the measurement controller 84 controls the second emitting circuit 42 for lighting the second lamp 41 pulsatively. The spectral intensity distribution $S_{w2}(\lambda)$ of the radiant light 11 from the standard non-fluorescent white sample 12 and the spectral intensity distribution $R_{w2}(\lambda)$ of the reference light 62 are respectively measured by the first and second spectroscopes 5 and 6 (Step #120). The measurement results are memorized in the RAM 82.

After that, the relative UV intensity of the illuminant is calibrated by using the standard fluorescent sample 13. The total spectral radiant factor $Bt_s(\lambda)$ of the standard fluorescent sample 13 illuminated by a predetermined illumination such as a standard D65 illuminant is known.

The standard fluorescent sample 13 is disposed at the sample aperture 21 of the integration sphere 2 (Step #130). The measurement controller 84 controls the first emitting circuit 32 for lighting the first lamp 31 pulsatively. The spectral intensity distribution $S_{O1}(\lambda)$ of the radiant light 11 from the standard fluorescent sample 13 and the spectral intensity distribution $R_{O1}(\lambda)$ of the reference light 62 are respectively measured by the first and second spectroscopes 5 and 6 (Step #140). The measurement results are memorized in the RAM 82.

Subsequently, the measurement controller 84 controls the second emitting circuit 42 for lighting second lamp 41 pulsatively. The spectral intensity distribution $S_{O2}(\lambda)$ of the radiant light 11 from the standard fluorescent sample 13 and the spectral intensity distribution $R_{O2}(\lambda)$ of the reference light 62 are respectively measured by the first and second spectroscopes 5 and 6 (Step #150). The measurement results are memorized in the RAM 82.

When the spectral intensity distributions are measured, the processor 85 calculates the first and second total spectral radiant factors $Bt_{S1}(\lambda)$ and $Bt_{S2}(\lambda)$ by the following equations (6) and using the data $S_{w1}(\lambda)$, $R_{w1}(\lambda)$, $S_{w2}(\lambda)$, $R_{w2}(\lambda)$, $S_{O1}(\lambda)$, $R_{O1}(\lambda)$, $S_{O2}(\lambda)$ and $R_{O2}(\lambda)$ memorized in the RAM 82 and the known reflection spectral radiant factor $Br_w(\lambda)$ memorized in the ROM 81 (Step #160).

$$Bt_{s1}(\lambda)=Br_w(\lambda)\cdot\{S_{O1}(\lambda)/R_{O1}(\lambda)\}/\{S_{w1}(\lambda)/R_{w1}(\lambda)\}$$

and $$Bt_{s2}(\lambda)=Br_w(\lambda)\cdot\{S_{O2}(\lambda)/R_{O2}(\lambda)\}/\{S_{w2}(\lambda)/R_{w2}(\lambda)\} \quad (6)$$

Subsequently, the processor 85 calculates a value $Bt_S(\lambda)$ by the following equation (7).

$$Bt_S(\lambda)=A(\lambda)\cdot Bt_{S1}(\lambda)+\{1-A(\lambda)\}\cdot Bt_{S2}(\lambda) \quad (7)$$

Hereupon, the value $Bt_S(\lambda)$ is calculated by linear combination of the weighted values of the first and second total spectral radiant factors $Bt_{S1}(\lambda)$ and $Bt_{S2}(\lambda)$, and it should be coincide with the known total spectral radiant factor $Bt_S(\lambda)$ of the standard fluorescent sample 13 which is memorized in the ROM 81. The value of the weight factor $A(\lambda)$ can directly be obtained by solving the above-mentioned equation (7).

When the calculated value coincides with the known total spectral radiant factor $Bt_S(\lambda)$, the most suitable value of the weight factor $A(\lambda)$ with respect to each wavelength $\lambda$ is set (Step #170). The value of the weight factor $A(\lambda)$ is memorized in the RAM 82. The setting of the weight factor $A(\lambda)$ is executed prior to the measurement of the fluorescent sample 1.

This embodiment is premised that the relative UV intensity distribution of the first illumination unit 3 has been varied in a time period from the setting of the weight factor $A(\lambda)$ to the measurement of the fluorescent sample 1. Under such the premise, the measured first total spectral radiant factor $Bt_1(\lambda)$ of the fluorescent sample 1 is corrected to a value $Bt_{O1}(\lambda)$ which is assumed that the florescent sample 1 is measured under the same illumination as that of the first illumination unit 3 when the weight factor $A(\lambda)$ is set.

The principle for correcting the variation of the relative spectral intensity distribution of the illuminant is described with reference to FIGS. 3A to 3D and 4A to 4B.

FIG. 3A shows an example of the spectral intensity distribution of the first illumination light from first illumination unit 3 when the weight factor $A(\lambda)$ is set. FIG. 3B shows an example of the spectral intensity distribution of the first illumination light from first illumination unit 3 when the fluorescent sample is measured. FIG. 3C shows an example of the spectral intensity distribution of the second illumination light from the second illumination unit 4 when the weight factor $A(\lambda)$ is set. FIG. 3D shows an example of the spectral intensity distribution of the second illumination light from the second illumination unit 4 when the fluorescent sample is measured. FIG. 4A shows an example of the spectral intensity distribution of the reference light 62 similar to that of the first illumination light when the weight factor $A(\lambda)$ is set. FIG. 4B shows an example of the spectral intensity distribution of the reference light 62 when the fluorescent sample 1 is measured.

Hereupon, the relative UV intensity distribution is normalization of the visible portion of the spectral intensity distribution by an integrated value of the UV portion of the spectral intensity distributions shown in FIGS. 3A and 3B. The variation of the fluorescent spectral radiant factor $Bf(\lambda)$ due to the variation of the relative UV intensity distribution is taken into account. However, the variation of the fluorescent spectral radiant factor $Bf(\lambda)$ of the radiant light 11 from the fluorescent sample 1 due to the variation of the spectral intensity distribution in the UV region of the illumination light is disregarded. In the latter case, the fluorescent spectral intensity distribution $$\int_{UV} I(\mu) \cdot F(\mu, \lambda) d\mu$$

in the above-mentioned equation (2) can be shown by the product of an integrated value E of the intensity of the illumination light in the UV region and a constant fluorescent spectral intensity distribution $F(\lambda)$. Hereupon, the integrated value E is shown by the following equation.

$$E = \int_{UV} I(\mu) d\mu$$

As shown in FIGs.3A and 3B, the spectral intensity distribution of the first illumination light from the first illumination unit 3 at the time of the setting of the weight factor $A(\lambda)$ is designated by $I_{01}(\lambda)$; the spectral intensity distribution of the first illumination light from the first illumination unit 3 at the time of the measurement of the fluorescent sample 1 is designated by $I_0(\lambda)$; the integrated value of the spectral intensity distribution in the UV region at the time of the setting of the weight factor $A(\lambda)$ is designated by a symbol "$E_0$"; and the integrated value of the spectral intensity distribution in the UV region at the time of the measurement of the fluorescent sample 1 is designated by a symbol "E".

The first total spectral radiant factor $Bt_{01}(\lambda)$ with respect to the visible region when the fluorescent sample 1 is assumed to be measured at the same time of setting the weight factor $A(\lambda)$ is shown by the following equation (8). The first total spectral radiant factor $Bt_1(\lambda)$ with respect to the visible region at the measurement of the fluorescent sample 1 is shown by the following equation (9).

$$Bt_{01}(\lambda) = Br(\lambda) + Bf_0(\lambda) = Br(\lambda) + E_0 \cdot F(\lambda)/L_{01}(\lambda) = Br(\lambda) + E_0 \cdot F(\lambda)/\{c(\lambda) \cdot I_{01}(\lambda)\} \quad (8)$$

$$Bt_1(\lambda) = Br(\lambda) + Bf(\lambda) = Br(\lambda) + E \cdot F(\lambda)/L_1(\lambda) = Br(\lambda) + E \cdot F(\lambda)/\{c(\lambda) \cdot I_1(\lambda)\} \quad (9)$$

Hereupon, the function $c(\lambda)$ is a function with respect to the wavelength $\lambda$ used for defining standardized illumination lights $L_{01}(\lambda)$ and $L_1(\lambda)$ by the following equations.

$$L_{01} = c(\lambda) \cdot I_{01}(\lambda)$$

and $$L_1(\lambda) = c(\lambda) \cdot I_0(\lambda)$$

On the other hand, the second total spectral radiant factor $Bt_{02}(\lambda)$ of the second illuminating light from the second illumination unit 4 at the setting of the weight factor $A(\lambda)$ and the second total spectral radiant factor $Bt_2(\lambda)$ of the second illumination light from the second illumination unit 4 at the measurement of the fluorescent sample 1 do not include the fluorescent spectral radiant factor $Bf(\lambda)$, since the UV component is removed from the second illumination light from the second illumination unit 4 by the UV cutoff filter 43. Thus, the second total spectral radiant factors $Bt_{02}(\lambda)$ and $Bt_2(\lambda)$ are respectively independent from the spectral intensity distribution of the illumination light, and it becomes $Bt_{02}(\lambda) = Bt_2(\lambda) = Br(\lambda)$.

When the both members of the above-mentioned equations (8) and (9) are subtracted, the following equation (10) is obtained.

$$Bt_{01}(\lambda) = Bt_1(\lambda) + F(\lambda)/c(\lambda) \cdot \{E_0/I_{01}(\lambda) - E/I(\lambda)\} \quad (10)$$

Hereupon, a relative UV intensity distribution $k_0(\lambda)$ and a relative UV intensity distribution $k(\lambda)$ shown by the following equations (11) are introduced. The relative UV intensity distribution $k_0(\lambda)$ is the normalization of the visible portion of the spectral intensity distribution $I_{01}(\lambda)$ of the first illumination light from the first illumination unit 3 at the setting of the weight factor $A(\lambda)$ by an integrated value $E_0$ of the UV portion of the spectral intensity distribution. The relative UV intensity distribution $k(\lambda)$ is the normalization of the visible portion of the spectral intensity distribution $I_{01}(\lambda)$ of the first illumination light from the first illumination unit 3 at the measurement of the fluorescent sample 1 by an integrated value E of the UV portion of the spectral intensity distributions.

$$k_0(\lambda) = I_{01}(\lambda)/E_0$$

$$k(\lambda) = I_1(\lambda)/E \quad (11)$$

When the equations (11) are substituted for the equation (10), the following equation (12) can be obtained.

$$Bt_{01}(\lambda) = Bt_1(\lambda) + F(\lambda)/c(\lambda) \cdot \{1/k_0(\lambda) - 1/k(\lambda)\} \quad (12)$$

When the relation $Bt_{02}(\lambda) = Bt_2(\lambda) = Br(\lambda)$ and the equation (11) are substituted for the above-mentioned equation (9), the following equation (13) can be obtained.

$$F(\lambda) = \{Bt_1(\lambda) - Bt_2(\lambda)\} \cdot c(\lambda) \cdot I(\lambda)/E = \{Bt_1(\lambda) - Bt_2(\lambda)\} \cdot c(\lambda) \cdot k(\lambda) \quad (13)$$

When the equation (13) is substituted for the equation (12), the following equation (14) can be obtained.

$$Bt_{01}(\lambda) = Bt_1(\lambda) + \{Bt_1(\lambda) - Bt_2(\lambda)\} \cdot \{k(\lambda)/k_0(\lambda)1\} \quad (14)$$

As can be seen from the equation (14), the corrected total spectral radiant factor $Bt_{01}(\lambda)$ can be obtained from the first and second total spectral radiant factors $Bt_1(\lambda)$ and $Bt_2(\lambda)$ at the measurement of the fluorescent sample 1 and the relative UV intensity distributions $k(\lambda)$ and $k_0(\lambda)$ in this embodiment.

The ratio of $k(\lambda)/k_0(\lambda)$ corresponds to a rate of change from the relative UV intensity distribution $k_0(\lambda)$ at the setting of the weight factor $A(\lambda)$ to the relative UV intensity distribution $k(\lambda)$ at the measurement of the fluorescent sample 1. Thus, the absolute values of the relative UV intensity distributions $k_0(\lambda)$ and $k(\lambda)$ are not necessarily so accurate.

Accordingly, it is possible to use the spectral intensity distributions $R_{01}(\lambda)$ and $R_1(\lambda)$ of the reference light 62 shown in FIGS. 4A and 4B instead of the spectral intensity distributions $I_{01}(\lambda)$ and $I_1(\lambda)$ of the first illumination light from the first illumination unit 3 shown in FIGS. 3A and 3B. In this modification, the absolute values of the spectral intensity distributions $R_{01}(\lambda)$ and $R_1(\lambda)$ are not necessarily so accurate. The error in the $k(\lambda)/k_0(\lambda)$ due to using $R_{01}(\lambda)$ and $R_1(\lambda)$ of the reference light 62 is not significant.

Figure 5:
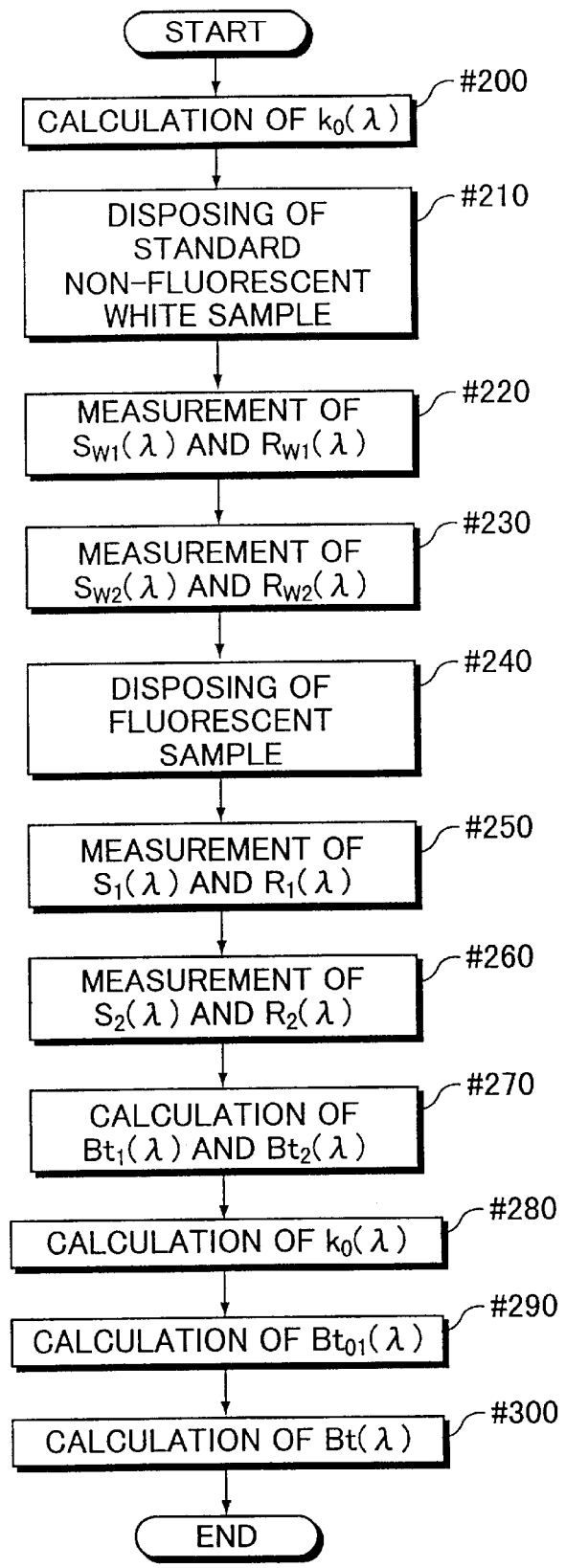
FIG. 5 is a flowchart for calculating a total spectral radiant factor of the fluorescent sample in the embodiment.

The process for obtaining the total spectral radiant factor $Bt(\lambda)$ of the fluorescent sample 1 is described with reference to FIGS. 1, 4 and 5. FIG. 5 is a flowchart showing the process.

At first, the processor 85 reads out the spectral intensity distribution $R_{01}(\lambda)$ of the reference light 62 from the RAM 82 which is memorized in the RAM 82 at the step #140 in the flowchart shown in FIG. 2. The spectral intensity distribution $R_{01}(\lambda)$ of the reference light 62 is similar to the spectral intensity distribution of the first illumination light from the first illumination unit 3. After that, the processor 85 calculates the relative UV intensity distribution $k_0(\lambda)$ by normalization of the visible portion of the spectral intensity distribution $R_{01}(\lambda)$ of the reference light 62 by an integrated value of the UV portion of the of the spectral intensity distribution $R_{01}(\lambda)$ of the reference light 62 (Step #200). The calculated relative UV intensity distribution $k_0(\lambda)$ is memorized in the RAM 82.

Concretely, the integration value $E_0$ of the UV portion of the spectral intensity distribution $R_{01}(\lambda)$ measurable by the second spectroscope 6, for example, a UV portion having the wavelength shorter than 400 nm ($\lambda$<400 nm) is calculated. In FIG. 4A, an area of the hatched region corresponds to the integrated value $E_0$. The integrated value $E_0$ is, for example, calculated by the following equation. Values in the parentheses designate the wavelength $\lambda$.

$$E_0 = R_{01}(360) + R_{01}(370) + R_{01}(380) + R_{01}(390)$$

Subsequently, the relative UV intensity distribution $k_0(\lambda)$ of the visible portion is calculated by the following equation, and the calculated relative UV intensity distribution $k_0(\lambda)$ is memorized in the RAM 82.

$$k_0(\lambda) = R_{01}(\lambda)/E_0 (\lambda \geq 400 \text{ nm})$$

The following steps #210 to #230 are substantially the same steps as the steps #100 to #120 in the flow shown in FIG. 2. That is, the white calibration of the apparatus is performed by measuring the non-fluorescent white sample 12, and the measured data $S_{w1}(\lambda)$, $R_{w1}(\lambda)$, $S_{w2}(\lambda)$ and $R_{w2}(\lambda)$ of the spectral intensity distributions are memorized in the RAM 82.

After that, the fluorescent sample 1 is disposed at the sample aperture 21 of the integration sphere 2 (Step #240). The measurement controller 84 controls the first emitting circuit 32 for lighting the first lamp 31 pulsatively. The spectral intensity distribution $S_1(\lambda)$ of the radiant light 11 from the fluorescent sample 1 and the spectral intensity distribution $R_1(\lambda)$ of the reference light 62 are respectively measured by the first and second spectroscopes 5 and 6 (Step #250). The measurement results are memorized in the RAM 82.

Subsequently, the measurement controller 84 controls the second emitting circuit 42 for lighting the second lamp 41 pulsatively. The spectral intensity distribution $S_2(\lambda)$ of the radiant light 11 from the fluorescent sample 1 and the spectral intensity distribution $R_2(\lambda)$ of the reference light 62 are respectively measured by the first and second spectroscopes (Step #260). The measurement results are memorized in the RAM 82.

When the spectral intensity distributions are measured, the processor 85 calculates the first and second total spectral radiant factors $Bt_1(\lambda)$ and $Bt_2(\lambda)$ by the following equations (15) and using the data $S_{w1}(\lambda)$, $R_{w1}(\lambda)$, $S_{w2}(\lambda)$, $R_{w2}(\lambda)$, $S_1(\lambda)$, $R_1(\lambda)$, $S_2(\lambda)$ and $R_2(\lambda)$ memorized in the RAM 82 and the known reflection spectral radiant factor $Br_w(\lambda)$ memorized in the ROM 81 (Step #270).

$$Bt_1(\lambda) = Br_w(\lambda) \cdot \{S_1(\lambda)/R_1(\lambda)\}/\{S_{w1}(\lambda)/R_{w1}(\lambda)\}$$

and $$Bt_2(\lambda) = Br_w(\lambda) \cdot \{S_2(\lambda)/R_2(\lambda)\}/\{S_{w2}(\lambda)/R_{w2}(\lambda)\} \quad (15)$$

Subsequently, the processor 85 calculates the relative UV intensity distribution $k(\lambda)$ by normalization of the visible portion of the spectral intensity distribution $R_1(\lambda)$ of the reference light 62 by an integrated value of the UV portion of the of the spectral intensity distribution $R_1(\lambda)$ of the reference light 62 (Step #280). The calculated relative UV intensity distribution $k(\lambda)$ is memorized in the RAM 82.

Concretely, the integration value E of the UV portion of the spectral intensity distribution $R_1(\lambda)$ measurable by the second spectroscope 6, for example, a UV portion having the wavelength shorter than 400 nm ($\lambda$<400 nm) is calculated. In FIG. 4B, an area of the hatched region corresponds to the integrated value E. The integrated value E is, for example, calculated by the following equation. Values in the parentheses designate the wavelength $\lambda$.

$$E = R_1(360) + R_1(370) + R_1(380) + R_1(390)$$

Subsequently, the relative UV intensity distribution $k(\lambda)$ of the visible portion is calculated by the following equation, and the calculated relative UV intensity distribution $k(\lambda)$ is memorized in the RAM 82.

$$k(\lambda) = R_1(\lambda)/E (\lambda \geq 400 \text{ nm})$$

Subsequently, the processor 85 calculates the corrected total spectral radiant factor $Bt_{01}(\lambda)$ by the above-mentioned equation (14) (Step #290). The calculated corrected total spectral radiant factor $Bt_{01}(\lambda)$ is memorized in the RAM 82.

That is, the corrected total spectral radiant factor $Bt_{01}(\lambda)$, which is similar to the first total spectral radiant factor $Bt_1(\lambda)$ of the same fluorescent sample 1 measured under the same illumination light from the first illumination unit 3 at the setting of the weight factor $A(\lambda)$, can be obtained from the ratio of the $k(\lambda)/k_0(\lambda)$ of the relative UV intensity distributions $k_0(\lambda)$ and $k(\lambda)$ and the first and second total spectral radiant factors $Bt_1(\lambda)$ and $Bt_2(\lambda)$.

After that, the processor 85 calculates the total spectral radiant factor $Bt(\lambda)$ of the fluorescent sample 1 from the corrected total spectral radiant factor $Bt_{01}(\lambda)$, the second total spectral radiant factor $Bt_2(\lambda)$ and the weight factor $A(\lambda)$ by the following equation (16) (Step #300).

$$Bt(\lambda) = A(\lambda) \cdot Bt_{01}(\lambda) + \{1 - A(\lambda)\} Bt_2(\lambda) \quad (16)$$

As mentioned above, the total spectral radiant factor $Bt(\lambda)$ of the fluorescent sample 1 can be obtained by using the corrected total spectral radiant factor $Bt_{01}(\lambda)$ which is similar to the first total spectral radiant factor $Bt_1(\lambda)$ of the same fluorescent sample 1 measured under the same illumination light from the first illumination unit 3 as that at the setting of the weight factor $A(\lambda)$. Thus, error component due to the variation of the relative UV intensity of the illuminant can largely be reduced, and the accuracy of the measurement of the spectral property of the fluorescent sample can be increased, even when the relative UV intensity distribution of the first illumination light from the first illumination unit 3 is varied from the setting of the weight factor $A(\lambda)$ to the measurement of the fluorescent sample 1.

Furthermore, the frequency of setting the weight factor $A(\lambda)$, that is the frequency for calibrating the relative UV intensity distribution can be decreased, so that the apparatus becomes useful. Still furthermore, the error component due to the variation of the illumination light by the effect of the integration sphere can be reduced with respect to the fluorescent sample 1 having a total spectral radiant factor $Bt(\lambda)$ which is largely different from that of the standard fluorescent sample 13 used for setting the weight factor $A(\lambda)$. Still furthermore, the relative UV intensity distribution can be calibrated accurately by using the standard fluorescent sample 13 in which the total spectral radiant factor $Bt_S(\lambda)$ is known.

Still furthermore, since the first and second total spectral radiant factors $Bt_1(\lambda)$ and $Bt_2(\lambda)$ respectively include the ratio of the radiant light radiated from the standard fluorescent sample 13 and the reference light at the same time as a component thereof, so that the affect due to the variation of the relative spectral intensity distribution of the lamps 31 and 41 can be removed. As a result, the weight factor $A(\lambda)$ can be obtained accurately.

Still furthermore, the apparatus shown in FIG. 1 has no mechanical movable element, so that the fluorescent sample 1 having a similar property to that of the standard fluorescent sample 13 can be measured during a very short time by memorizing the weight factor $A(\lambda)$ obtained by using the standard fluorescent sample 13 and the spectral intensity distribution $R_{O1}(\lambda)$ of the reference light 62 of the first illumination unit 3 simultaneously measured and memorized in the RAM 82.

Still furthermore, when the fluorescent sample 1 to be measured has a spectral fluorescent property which is the same as or similar to that of the standard fluorescent sample 13, for example, the fluorescent sample 1 includes the same or similar fluorescent pigment or fluorescent dye, the total spectral radiant factor $Bt(\lambda)$ of the fluorescent sample 1 becomes substantially the same as that supposed to be obtained if it is illuminated by the same illumination which illuminated the standard fluorescent sample 13. Thus, all the values with respect to the color calculated from the total spectral radiant factor $Bt(\lambda)$ of the fluorescent sample 1 can be coincided with the values when the same fluorescent sample is illuminated by a predetermined light such as the standard D65 illuminant.

Figure 9:
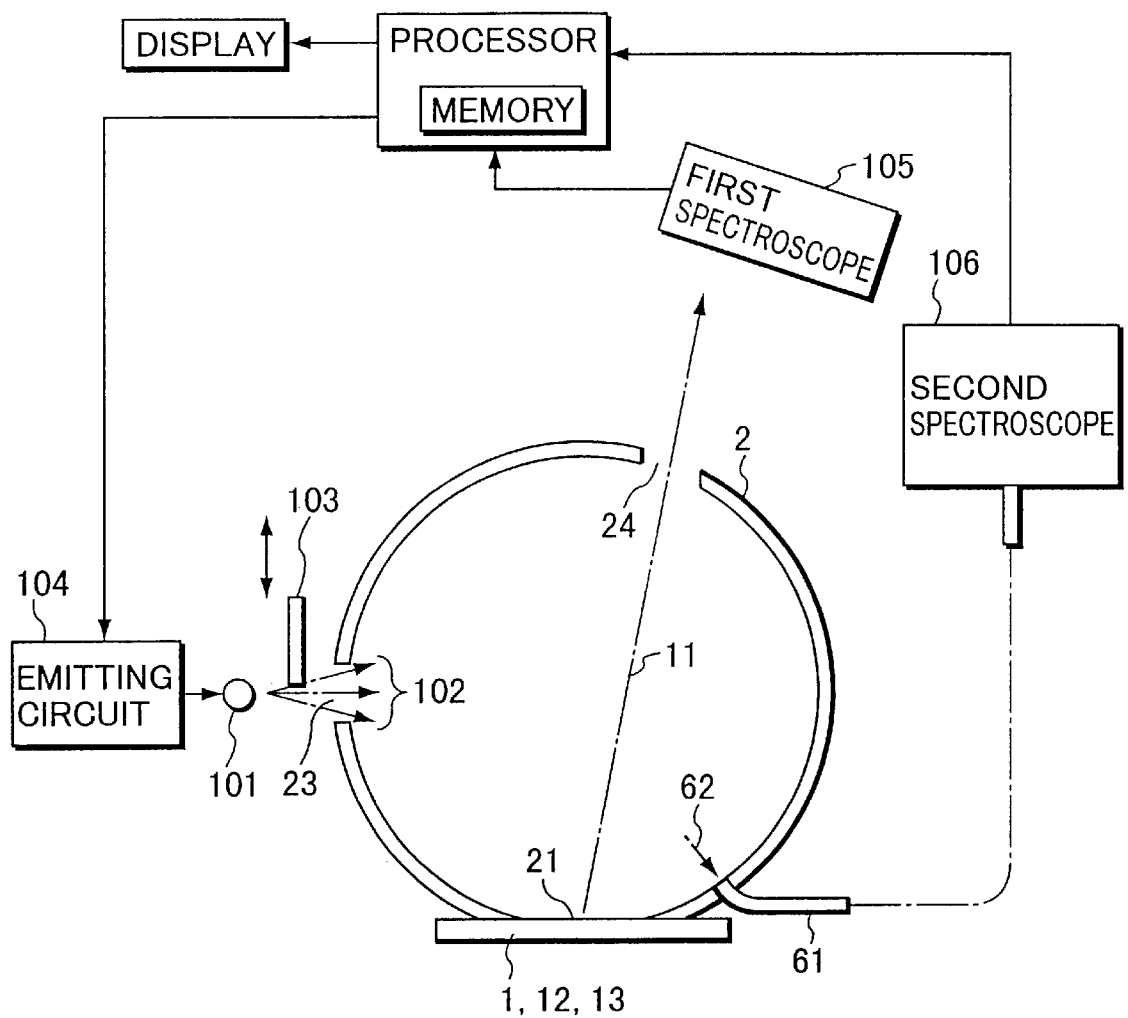
FIG. 9 is the cross-sectional front view showing the configuration of the conventional apparatus for measuring spectral property of a fluorescent sample.
Figure 10:
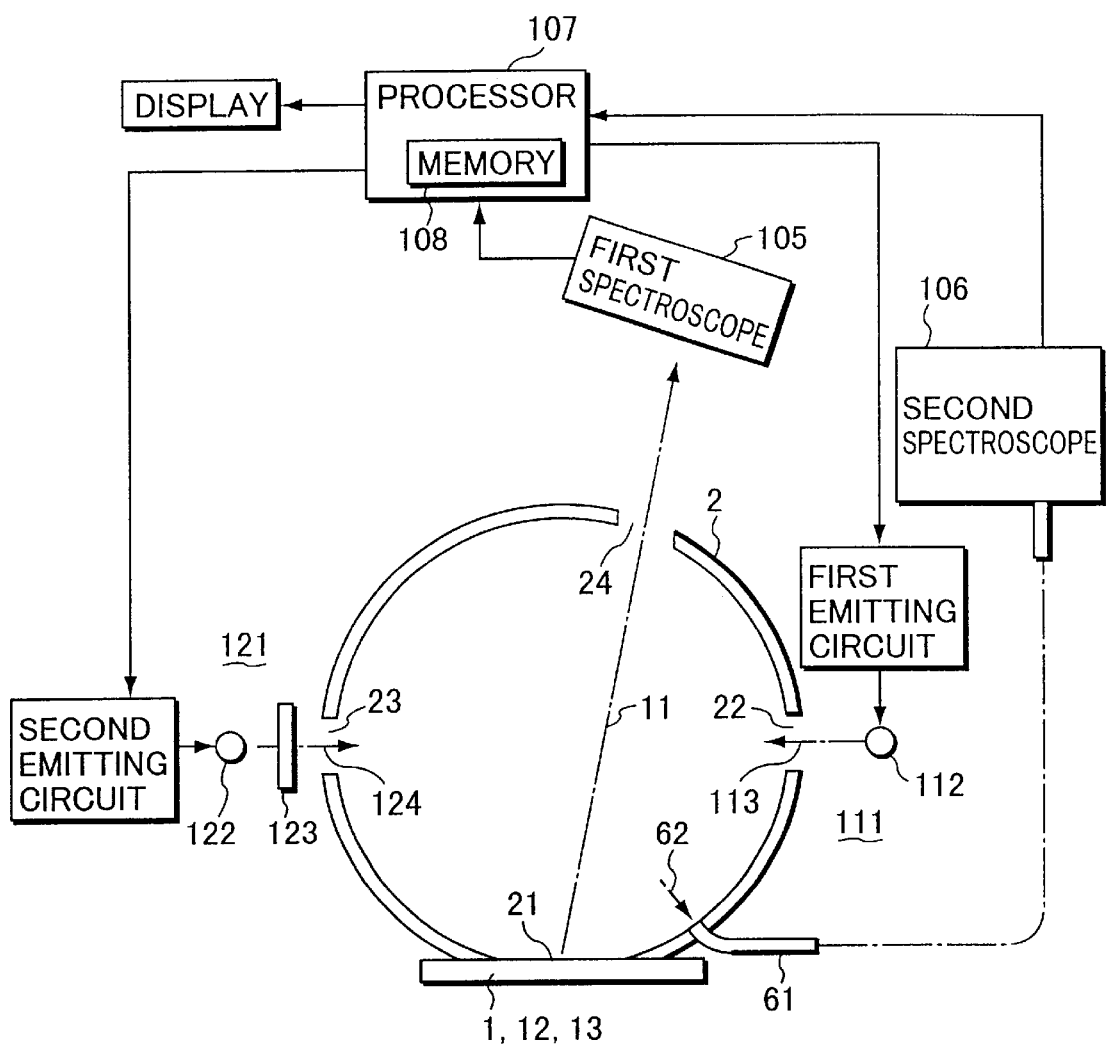
FIG. 10 is the cross-sectional front view showing the configuration of another conventional apparatus for measuring spectral property of the fluorescent sample.

By the way, the reflection spectral radiant factor $Br(\lambda)$ is independent from the spectral intensity distribution of the illumination light. On the other hand, the fluorescent spectral radiant factor $Bf(\lambda)$ depends on the spectral intensity distribution of the illumination light, especially, in the UV region, so that the value of the fluorescent spectral radiant factor $Bf(\lambda)$ owing to the first illumination light from the first illumination unit 3 is largely different from that owing to the second illumination light from the second illumination unit 4. Thus, the linear combination of the corrected spectral radiant factor $Bt_{O1}(\lambda)$ and the second spectral radiant factor $Bt_2(\lambda)$ with using the weight factor $A(\lambda)$ depending on the wavelength $\lambda$ means the adjustment of the relative intensity of the fluorescent spectral radiant factor $Bf(\lambda)$ in the visible region where the fluorescence is existing the fluorescent light against the reflection spectral radiant factor $Br(\lambda)$ with respect to each wavelength $\lambda$. This correction is equivalent to the adjustment of the relative UV intensity by changing the insertion rate of the UV cutoff filter as shown in FIG. 9. At this time, the above-mentioned equation (4) is modified to the following equation.

$$Bf(\lambda) = \int_{UV} P(\lambda) \cdot I(\mu) \cdot E(\mu, \lambda) d\mu / L(\lambda)$$

Hereupon, $P(\lambda)$ is a reduction factor of the UV intensity depending on the wavelength $\lambda$ of the observation in the visible region.

Examples of the spectral intensity distribution of the illumination light, which is the weighted linear combination of the corrected total spectral radiant factor $Bt_{O1}(\lambda)$ owing to the first illumination light from the first illumination unit 3 and the second spectral radiant factor $Bt_2(\lambda)$ owing to the second illumination unit 4 by the weight factor $A(\lambda)$ are shown in FIGS. 6A to 6E. For simplifying the explanation, the weigh factor $A(\lambda)$ is a constant value independent from the wavelength.

FIG. 6A shows the spectral intensity distribution $I_1(\lambda)$ of the first illumination light from the first illumination unit 3. FIG. 6B shows the spectral intensity distribution $I_2(\lambda)$ of the second illumination light from the second illumination unit 4. FIG. 6C shows the linearly composed spectral intensity distribution $A_1 \cdot I_1(\lambda) + (1-A_1) \cdot I_2(\lambda)$ of the illumination light when the weight factor $A(\lambda) = A_1 < 1$. FIG. 6D shows the linearly composed spectral intensity distribution $A_2 \cdot I_1(\lambda) + (1-A_2) \cdot I_2(\lambda)$ of the illumination light when the weight factor $A(\lambda) = A_2 > 1$. FIG. 6E shows the linearly composed spectral intensity distribution $A_3 \cdot I_1(\lambda) + (1-A_3) \cdot I_2(\lambda)$ of the illumination light when the weight factor $A(\lambda) = A_3 < A_1 < 1$.

In this embodiment, a spectral intensity distribution of an illumination light giving an objective total spectral radiant factor is obtained by setting a suitable weight factor $A(\lambda)$ with respect to each wavelength. For example, a spectral intensity $A(\lambda_2) \cdot I_1(\lambda_2) + \{1 - A(\lambda_2)\} \cdot I_2(\lambda_2)$ with respect to a predetermined wavelength $\lambda_2$ of the linearly composed illumination light is calculated by using the weight factor $A(\lambda_2) = A_2$. A spectral intensity $A(\lambda_3) \cdot I_1(\lambda_3) + \{1 - A(\lambda_3)\} \cdot I_2(\lambda_3)$ with respect to another predetermined wavelength $\lambda_3$ of the linearly composed illumination light is calculated by using the weight factor $A(\lambda_3) = A_3$. The same procedure is applied to the remaining wavelength. In the figures, the symbol $S_{UV}$ designates an area of the spectral intensity distribution in a region having the wavelength shorter than 400 nm corresponding to all the UV region.

Figure 7A:
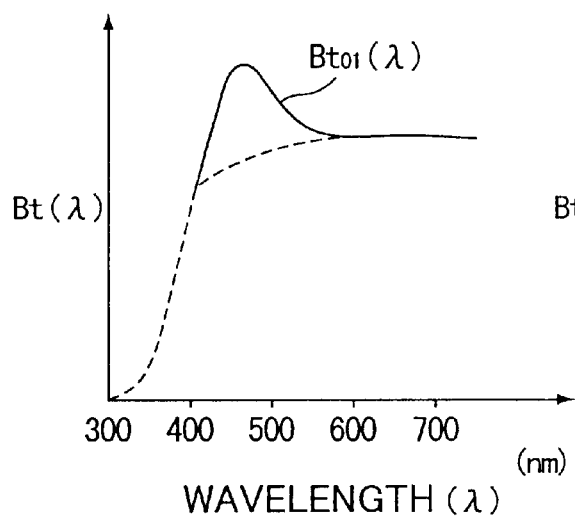
FIG. 7A is a graph showing a corrected total spectral radiant factor when the sample is illuminated by a first illumination light from the first illumination unit.
Figure 7B:
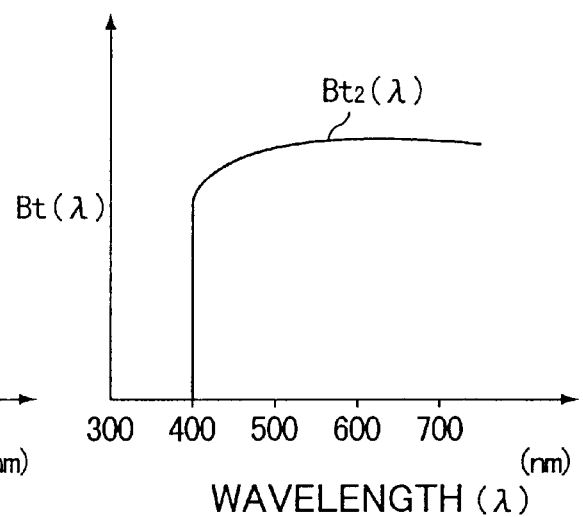
FIG. 7B is a graph showing a second total spectral radiant factor when the sample is illuminated by a second illumination light from the second illumination unit.
Figure 7C:
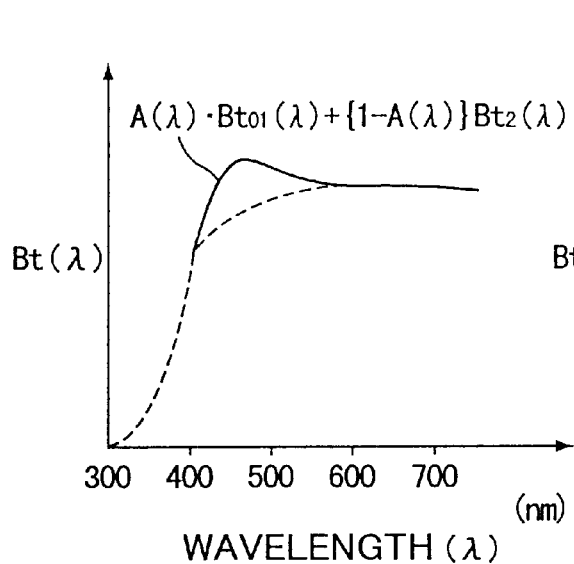
FIG. 7C is a graph showing a composed total spectral radiant factor corresponding to FIG. 6C.
Figure 7D:
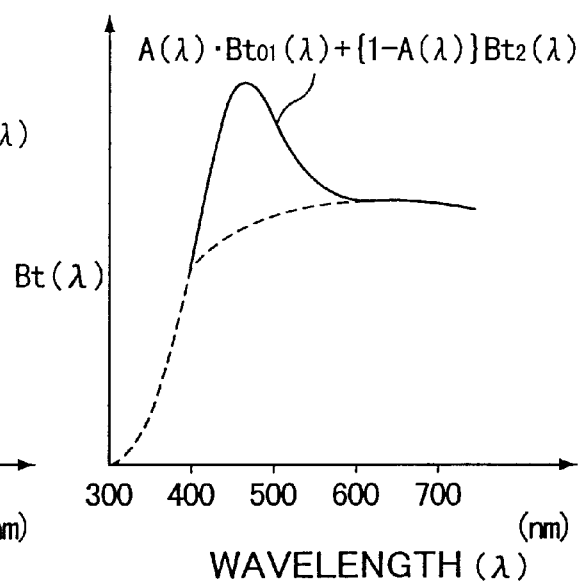
FIG. 7D is a graph showing a composed total spectral radiant factor corresponding to FIG. 6D.

The total spectral radiant factor $Bt(\lambda)$ with respect to the illuminations having the spectral intensity distributions shown in FIGS. 6A to 6D are shown in FIGS. 7A to 7D. FIG. 7A shows the corrected total spectral radiant factor $Bt_{O1}(\lambda)$ when the sample is illuminated by the first illumination light from the first illumination unit 3. FIG. 7B shows the second total spectral radiant factor $Bt_2(\lambda)$ when the sample is illuminated by the second illumination light from the second illumination unit 4. FIG. 7C shows the composed total spectral radiant factor $Bt(\lambda)$ which is calculated by the above-mentioned equation (16) when the weight factor $A(\lambda) = A_1$ in FIG. 6C is applied to the corrected total radiant factor $Bt_{O1}(\lambda)$ shown in FIG. 6A and the second total spectral radiant factor $Bt_2(\lambda)$ shown in FIG. 6B. FIG. 7D shows the composed total spectral radiant factor $Bt(\lambda)$ which is calculated by the above-mentioned equation (16) when the weight factor $A(\lambda) = A_2$ in FIG. 6D is applied to the corrected total spectral radiant factor $Bt_{O1}(\lambda)$ shown in FIG. 6A and the second total spectral radiant factor $Bt_2(\lambda)$ shown in FIG. 6B.

In comparison with FIG. 6A and FIG. 6C, an integrated value $A_1 \cdot S_{UV}$ of the spectral intensity in the UV region shown in FIG. 6C is smaller than the integrated value $S_{UV}$ of the spectral intensity in the UV region of the spectral intensity distribution $I_1(\lambda)$ shown in FIG. 6A. However, the visible portion of the spectral intensity distribution $I(\lambda)$ shown in FIG. 6C is substantially the same as that of the spectral intensity distribution $I_1(\lambda)$ shown in FIG. 6A. Thus, a ratio $A_1 \cdot S_{UV}/I(\lambda)$ of the integrated value $A_1 \cdot S_{UV}$ against the spectral intensity distribution $I(\lambda)$ in FIG. 6C is larger than a ratio $S_{UV}/I_1(\lambda)$ of the integrated value $S_{UV}$ against the spectral intensity distribution $I_1(\lambda)$ in FIG. 6A. That is, $\{A_1 \cdot S_{UV}/I(\lambda)\} < \{S_{UV}/I_1(\lambda)\}$.

Similarly, in comparison with FIG. 6A and FIG. 6D, an integrated value $A_2 \cdot S_{UV}$ of the spectral intensity in the UV region shown in FIG. 6D is larger than the integrated value $S_{UV}$ shown in FIG. 6A. However, the visible portion of the spectral intensity distribution $I(\lambda)$ shown in FIG. 6D is substantially the same as that of the spectral intensity distribution $I_1(\lambda)$ shown in FIG. 6A. Thus, a ratio $A_2 \cdot S_{UV}/I(\lambda)$ of the integrated value $A_2 \cdot S_{UV}$ against the spectral intensity distribution $I(\lambda)$ in FIG. 6D is smaller than the ratio $S_{UV}/I_1(\lambda)$ of the integrated value $S_{UV}$ against the spectral intensity distribution $I_1(\lambda)$ in FIG. 6A. That is, $\{A_2 \cdot S_{UV}/I(\lambda)\} > \{S_{UV}/I_1(\lambda)\}$.

As mentioned above, a composed illumination light in which the ratio of the spectral intensity in the total UV region against the spectral intensity distribution with respect to the wavelength $\lambda$ in the visible region can be adjusted to a targeted value by using the first and second illumination units 3 and 4 and the weight factor $A(\lambda)$.

A modification of an apparatus in this embodiment is described with reference to FIG. 8. The modified apparatus has a single illumination unit 9 instead of the first and second illumination units 3 and 4 shown in FIG. 1. The illumination unit 9 comprises a lamp 91, an emission circuit 92, a cutoff filter 93 and a driver 94 for driving the cutoff filter 93.

The lamp 91 such as a xenon flash lamp emitting a light flux including a UV component is disposed in the vicinity of the illuminant aperture 25 of the integration sphere 2. The emitting circuit 92 drives the lamp 91 for generating pulsating light flux 95. The light flux 95 enters into the integration sphere 2 through the illuminant aperture 25.

The UV cutoff filter 93 is movably provided for taking a first position on an optical path of the light flux 95 illuminated by solid line and a second position completely evacuated from the optical path of the light flux 95 illuminated by dotted line between the lamp 91 and the illuminant aperture 25. The UV cutoff filter 93 transmits only a light flux having a wavelength longer than a predetermined cutoff wavelength $\lambda_{C1}$ (for example, $\lambda_{C1}=400$ nm). Thus, the UV light flux having the wavelength shorter than the cutoff wavelength $\lambda_{C1}$ can be removed from the light flux 95 emitted by the lamp 91 when the UV cutoff filter 93 is positioned at the first position. The driver 94 connected to the measurement controller 84 moves the cutoff filter between the first position and the second position.

When the UV cutoff filter 93 is positioned at the second position, the illumination unit 9 serves substantially the same function as the first illumination unit 3 shown in FIG. 1. Alternatively, when the UV cutoff filter 93 is disposed at the first position, the illumination unit 9 serves substantially as the same function as the second illumination unit 4 shown in FIG. 1.

The measurement controller 84 controls the driver 94 for positioning the cutoff filter 93 at alternative of the first position and the second position, and controls the emitting circuit 92 for pulsatively lighting the lamp 91 when the cutoff filter 93 is positioned at the first or second position. Furthermore, the measurement controller 84 memorizes the data of the spectral intensity distribution from the first and second spectroscopes 5 and 6 into the RAM 82.

The processor 85 calculates the first total spectral radiant factor $Bt_1(\lambda)$ of the illumination light including the UV component, and the second total spectral radiant factor $Bt_2(\lambda)$ of the illumination light without the UV component. Furthermore, the processor 85 calculates the corrected total spectral radiant factor $Bt_{01}(\lambda)$ from the first total spectral radiant factor $Bt_1(\lambda)$. Finally, the processor 85 calculates the total spectral radiant factor $Bt(\lambda)$ of the fluorescent sample from the corrected spectral radiant factor $Bt_{01}(\lambda)$ and the second total spectral radiant factor $Bt_2(\lambda)$.

Figure 8:
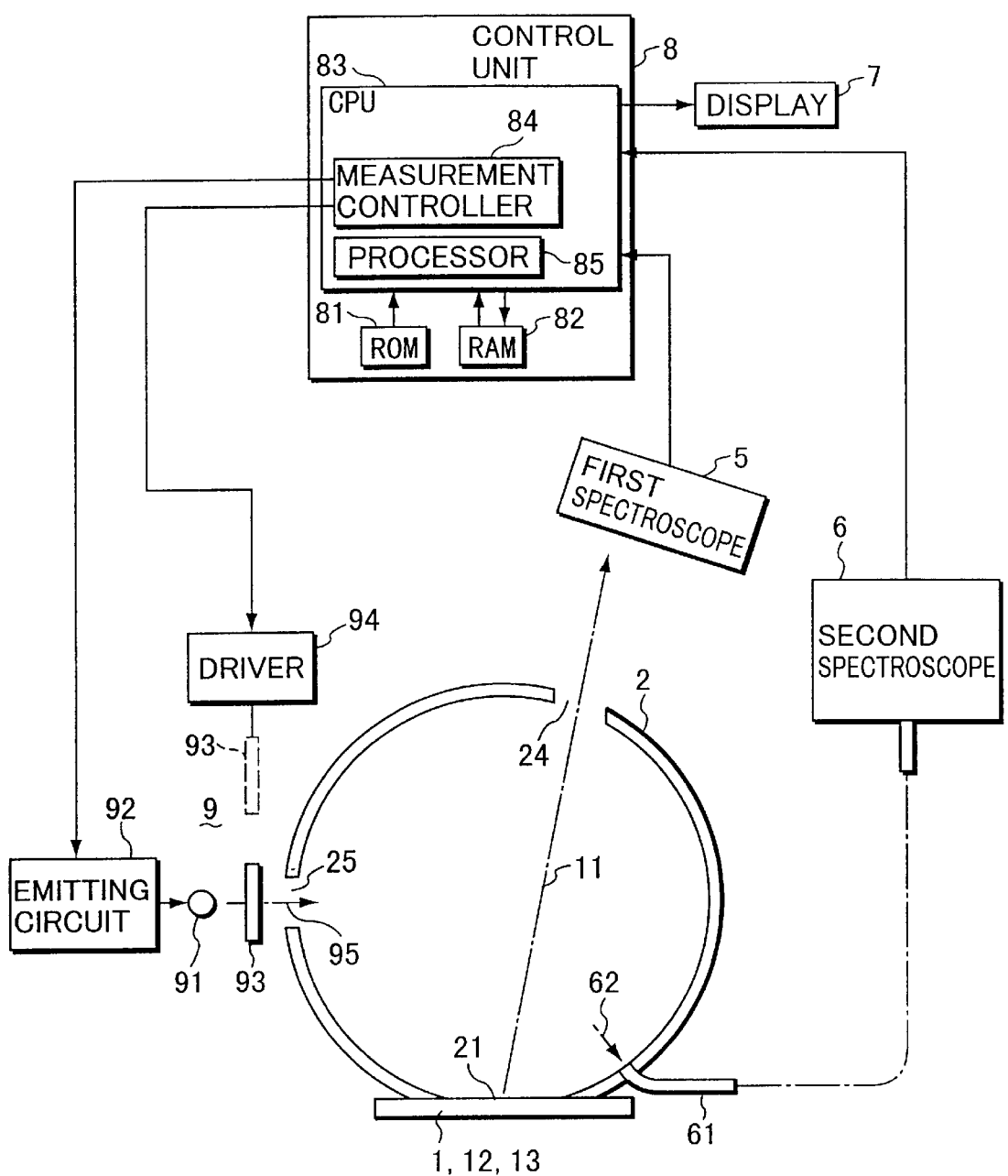
FIG. 8 is a cross-sectional front view showing a modified configuration of the embodiment of the apparatus for measuring spectral property of the fluorescent sample.

As can be seen from FIG. 8, this modification has substantially the same mechanical construction as the conventional apparatus shown in FIG. 9 having a mechanism for adjusting the insertion ratio of the UV cutoff filter. In other words, this invention can easily be applied to the conventional apparatus by changing the procedure of the measurement and the calculation of the conventional methods to the methods described in the above mentioned embodiment. As a result, the spectral property such as the total spectral radiant factor of the fluorescent sample can be obtained precisely.

In the above-mentioned description, the total spectral radiant factor $Bt(\lambda)$ of the fluorescent sample is obtained precisely by setting the weight factor $A(\lambda)$ and calculating the corrected total spectral radiant factor $Bt_{01}(\lambda)$ which is equivalent to the total spectral radiant factor of the fluorescent sample when the fluorescent sample is illuminated by the same illumination light including the UV component at the setting of the weight factor $A(\lambda)$. The spectral property to be measured by this invention, however, is not restricted by the above-mentioned total spectral radiant factor $Bt(\lambda)$.

Visual property of the white fluorescent sample such as a cloth or a paper including fluorescent whitening agent is represented by, for example, CIE whiteness and tint. Furthermore, there is a standard fluorescent sample 13 in which the CIE whiteness and tint thereof is known. Thus, it is possible to modify the above-mentioned embodiment to the follows.

A standard fluorescent sample 13, in which the CIE whiteness and tint thereof when it is illuminated by the predetermined illumination light such as the standard D65 illuminant, is used. The values of the CIE whiteness and the tint are memorized in the ROM 81 shown in FIG. 1.

The CIE whiteness "WI" and tint "Tint" are calculated by the following equations.

$$X = \int \bar{x}(\lambda) \cdot Bt(\lambda) d\lambda$$

$$Y = \int \bar{y}(\lambda) \cdot Bt(\lambda) d\lambda$$

$$Z = \int \bar{z}(\lambda) \cdot Bt(\lambda) d\lambda$$

The $\bar{x}(\lambda)$, $\bar{y}(\lambda)$ and $\bar{z}(\lambda)$ are respectively color matching functions of a standard observer defined by the CIE, the $Bt(\lambda)$ is the total spectral radiant factor of the sample, and X, Y and Z are the tristimulus values of the sample.

$$x = X/(X+Y+Z)$$

$$y = Y/(X+Y+Z)$$

$$x_n = X_n/(X_n+Y_n+Z_n)$$

$$y_n = Y_n/(X_n+Y_n+Z_n)$$

The symbols "$X_n$", "$Y_n$" and "$Z_n$" designate the tristimulus values of the illumination light, the symbols "x" and "y" designate the color values of the sample and the symbols "$x_n$" and "$y_n$" designates the color values of the illumination light.

$$WI = Y + 800(x_n - x) + 1700(y_n - y)$$

$$\text{Tint} = 900(x_n - x) - 650(y_n - y)$$

In this modification, the weight factor $A(\lambda)$ is defined by the equation $A(\lambda) = F(\lambda, a, b)$. Hereupon, the function $F(\lambda, a,$ b) designates a function of the wavelength λ defined by two constant values "a" and "b".

The processor 85 calculates the total spectral radiant factor Bt(λ) by the above-mentioned equation (16). Subsequently, the processor 85 calculates the CIE whiteness and the tint from the total spectral radiant factor Bt(λ). When the calculated value of the CIE whiteness and the tint are not coincided with the values given with the standard fluorescent sample 13, the processor repeats the calculation with changing the values of the constant values "a" and "b" until the calculated values is coincided with or similar to the given values.

As an example of the function F(λ, a, b), a linear function F(λ, a, b)=a·λ+b can be used for simplifying the calculation of the weight factor A(λ).

In this modification, the weight factor A(λ) is not set in a manner so that the calculated total spectral radiant factor Bt(λ) of the standard fluorescent sample is coincided with the known total spectral radiant factor $Bt_S(\lambda)$ measured under the standard illumination light. Thus, another color value such as CIE color value or L*a*b* color value which is obtained from the total spectral radiant factor Bt(λ) is not necessarily obtained accurately. It, however, is possible to close the calculated total spectral radiant factor Bt(λ) of the standard fluorescent sample to the known total spectral radiant factor $Bt_S(\lambda)$ by using a more suitable function corresponding to the difference of the spectral intensity distributions of the illumination light from the first and second illumination unit 3 and 4 from that of the standard illumination light for measurement such as the standard D65 illuminant as the function F(λ, a, b). In the latter case, the other color values can be obtained accurately.

In the above-mentioned embodiment, the weight factor A(λ) which is depend on the wavelength is used. It, however, is possible to obtain another weigh factor α which is independent from the wavelength by measuring one or more indexes such as the CIE whiteness or the CIE color value of the standard fluorescent sample in which the values of the indices measured under the standard illumination light are known.

In this case, the weight factor α is calculated by the following equation instead of the above-mentioned equation (7) in a manner so that the index calculated from the total spectral radiant factor $Bt_S(\lambda)$ becomes close to the known values of them.

$$Bt_S(\lambda)=\alpha \cdot Bt_{S1}(\lambda)+(1-\alpha) \cdot Bt_{S2}(\lambda)$$

The calculation method of the weight factor α in this modification is similar to the adjustment of the insertion ratio of the UV cutoff filter in the conventional apparatus shown in FIG. 9. However, there is no mechanically moving element in the apparatus of this modification in comparison with the conventional apparatus, so that the configuration of the apparatus becomes simple and the time for calibrating the apparatus becomes shorter. As a result, the workability of the measurement of the fluorescent sample can be increased.

The calibration of the relative UV intensity in this embodiment is numerically executed by using the weight factor. Thus, it is preferable that a plurality of weight factors $A_D(\lambda), A_A(\lambda), A_F(\lambda)$ corresponding to a plurality of standard illumination lights such as the standard D65, A and F illuminants are previously calculated and memorized in the memory. By such a configuration, all the total spectral radiant factors and the color values of the same sample with respect to all the standard illumination lights can be obtained by only one measurement. As a result, the same sample can be estimated by a plurality of the standard illumination lights.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. An apparatus for measuring a spectral property of a fluorescent sample including a fluorescent material comprising:

a first illumination unit for emitting a first illumination light including a ultraviolet component;

a second illumination unit for emitting a second illumination light including a component having a wavelength longer than a predetermined cutoff wavelength;

a first spectroscope for measuring a spectral intensity distribution of a radiant light radiated from a sample disposed at a measurement position when the sample is illuminated by the first or second illumination light;

a second spectroscope for measuring a spectral intensity distribution of a reference light which is similar to the first or second illumination light when the sample is illuminated by the first or second illumination light;

a memory memorizing a weight factor;

a measurement controller alternatively controlling the first and second illumination units for illuminating a fluorescent sample to be measured at the measurement position, controlling the first spectroscope for measuring alternative of a first measured radiant light spectral intensity distribution of a radiant light radiated from the fluorescent sample corresponding to the first illumination light and a second measured radiant light spectral intensity distribution of a radiant light radiated from the fluorescent sample corresponding to the second illumination light, and controlling the second spectroscope for measuring alternative of a first measured reference light spectral intensity distribution of a reference light corresponding to the first illumination light and a second measured reference light spectral intensity distribution of a reference light corresponding to the second illumination light;

a first processor for calculating a first total spectral radiant factor of the fluorescent sample by using the first measured radiant light spectral intensity distribution and the first measured reference light spectral intensity distribution, and a second total spectral radiant factor of the fluorescent sample by using the second measured radiant light spectral intensity distribution and the second measured reference light spectral intensity distribution;

a second processor for calculating a corrected total spectral radiant factor by using a ratio of an intensity in a visible portion of the first standard reference light spectral intensity distribution against an intensity in a ultraviolet portion thereof when the weight factor is obtained, and a ratio of an intensity in a visible portion of the first measured reference light spectral intensity distribution against an intensity in a ultraviolet portion thereof; and a third processor for calculating a total spectral radiant factor of the fluorescent sample by using the corrected total spectral radiant factor, the second total spectral radiant factor and the weight factor.

2. The apparatus in accordance with claim 1, wherein
the second processor calculates the corrected total spectral radiant factor by following equation;

$$Bt_{O1}(\lambda)=Bt_1(\lambda)+\{Bt_1(\lambda)-Bt_2(\lambda)\}\cdot\{k(\lambda)/k_0(\lambda)-1\}$$

- $Bt_{O1}(\lambda)$: the corrected total spectral radiant intensity of the fluorescent sample;
- $Bt_1(\lambda)$: the first total spectral radiation factor of the fluorescent sample;
- $Bt_2(\lambda)$: the second total spectral radiation factor of the fluorescent sample;
- $k(\lambda)$: a relative ultraviolet(UV) intensity distribution that a visible portion of the first measured reference light spectral intensity distribution normalized by an integrated value of a UV portion thereof;
- $k_0(\lambda)$: a relative ultraviolet(UV) intensity distribution that a visible portion of the first standard reference light spectral intensity distribution normalized by an integrated value of a UV portion thereof; and the third processor calculates the total spectral radiant factor of the fluorescent sample by the following equation;

$$Bt(\lambda)=\alpha\cdot Bt_{O1}(\lambda)+(1-\alpha)\cdot Bt_2(\alpha)$$

- $Bt(\lambda)$: the total spectral radiant factor of the fluorescent sample;
- $\alpha$: the weight factor;
- $Bt_{O1}(\lambda)$: the corrected total spectral radiant intensity of the fluorescent sample;
- $Bt_2(\lambda)$: the second total spectral radiation factor of the fluorescent sample.

3. The apparatus in accordance with claim 2 further comprising a fourth processor for calculating the weight factor from a first and a second standard reference light spectral intensity distributions of reference lights and a first and a second standard radiant light spectral intensity distributions of radiant lights radiated from the standard fluorescent sample when a standard fluorescent sample disposed at the measurement position is illuminated by the first and second illumination lights; and a memory controller for memorizing the calculated weight factor into the memory.

4. The apparatus in accordance with claim 3, wherein
the measurement controller alternatively controls the first and second illumination units for illuminating the standard fluorescent sample in which a predetermined total spectral radiant factor of that illuminated by an illumination light having a predetermined relative UV intensity is known, controls the first spectroscope for measuring alternative of the first standard radiant light spectral intensity distribution of a radiant light radiated from the standard fluorescent sample corresponding to the first illumination light and the second standard radiant light spectral intensity distribution of a radiant light radiated from the standard fluorescent sample corresponding to the second illumination light, and controls the second spectroscope for measuring alternative of the first standard reference light spectral intensity distribution of a reference light corresponding to the first illumination light and the second standard reference light spectral intensity distribution of a reference light corresponding to the second illumination light;

the fourth processor further calculates a first total spectral radiant factor of the standard fluorescent sample from the first standard radiant light spectral intensity distribution and the first standard reference light spectral intensity distribution, and a second total spectral radiant factor of the standard fluorescent sample from the second standard radiant light spectral intensity distribution and the second standard reference light spectral intensity distribution, and sets a weight factor $A(\lambda)$ with respect to each wavelength in a manner to satisfy the following equation:

$$Bt_S(\lambda)=A(\lambda)\cdot Bt_{S1}(\lambda)+\{1-A(\lambda)\}\cdot Bt_{S2}(\lambda)$$

- $Bt_S(\lambda)$: the total spectral radiant factor of the standard fluorescent sample;
- $A(\lambda)$: the weight factor $\alpha$ set with respect to each wavelength;
- $Bt_{S1}(\lambda)$: the first total spectral radiant factor of the standard fluorescent sample;
- $Bt_{S2}(\lambda)$: the second total spectral radiant factor of the standard fluorescent sample; and the memory controller memorizes the first standard reference light spectral intensity distribution into the memory.

5. The apparatus in accordance with claim 3, wherein
the measurement controller alternatively controls the first and second illumination units for illuminating the standard fluorescent sample in which a predetermined index calculated from a total spectral radiant factor of that illuminated by an illumination light having a predetermined relative UV intensity is known, controls the first spectroscope for measuring alternative of the first standard radiant light spectral intensity distribution of a radiant light radiated from the standard fluorescent sample corresponding to the first illumination light and the second standard radiant light spectral intensity distribution of a radiant light radiated from the standard fluorescent sample corresponding to the second illumination light, and controls the second spectroscope for measuring alternative of the first standard reference light spectral intensity distribution of a reference light corresponding to the first illumination light and the second standard reference light spectral intensity distribution of a reference light corresponding to the second illumination light;

the fourth processor further calculates a first total spectral radiant factor of the standard fluorescent sample from the first standard radiant light spectral intensity distribution and the first standard reference light spectral intensity distribution, and a second total spectral radiant factor of the standard fluorescent sample from the second standard radiant light spectral intensity distribution and the second standard reference light spectral intensity distribution, and sets the weight factor $\alpha$ in a manner to satisfy the following equation;

$$Bt_S(\lambda)=\alpha\cdot Bt_{S1}(\lambda)+(1-\alpha)\cdot Bt_{S2}(\lambda)$$

- $Bt_S(\lambda)$: the total spectral radiant factor of the standard fluorescent sample;
- $\alpha$: the weight factor;
- $Bt_{S1}(\lambda)$: the first total spectral radiant factor of the standard fluorescent sample;
- $Bt_{S2}(\lambda)$: the second total spectral radiant factor of the standard fluorescent sample; and the memory controller memorizes the first standard reference light spectral intensity distribution into the memory.

6. The apparatus in accordance with claim 1, wherein the cutoff frequency is the shortest wavelength of the visible light.

7. The apparatus in accordance with claim 1 further comprising an index processor for calculating an index with respect to a color from the total spectral radiant factor calculated by the third processor.

8. The apparatus in accordance with claim 1 further comprising a display for displaying an information with respect to the total spectral radiant factor calculated by the third processor.

9. A method for measuring a spectral property of a fluorescent sample comprising:

a first step for obtaining a weight factor from a first and second standard radiant light spectral intensity distributions of radiant lights radiated from a predetermined standard fluorescent sample disposed at a measurement position and a first and second standard reference light spectral intensity distributions of reference lights similar to those of a first and second illumination lights when the standard fluorescent sample is alternatively illuminated by the first illumination light including a ultraviolet component and the second illumination light including a component having a wavelength longer than a predetermined cutoff wavelength;

a second step for obtaining a first and second total spectral radiant factors of a fluorescent sample to be measured disposed at the measurement position from the first and second measured radiant light spectral intensity distributions of radiant lights radiated from the fluorescent sample and a first and a second measured reference light spectral intensity distributions of reference lights when the fluorescent sample is alternatively illuminated by the first and second illumination lights;

a third step for correcting the first total spectral radiant factor by using a ratio of an intensity in a visible portion of the first standard reference light spectral intensity distribution against an intensity in a ultraviolet portion thereof and a ratio of an intensity in a visible portion of the first measured reference light spectral intensity distribution against an intensity in a ultraviolet portion thereof; and a fourth step for calculating a total spectral radiant factor of the fluorescent sample from the corrected first total spectral radiant factor, the second total spectral radiant factor and the weight factor.

10. The method in accordance with claim 9, wherein the third step corrects the first total spectral radiant factor by the following equation of $$Bt_{O1}(\lambda)=Bt_1(\lambda)+\{Bt_1(\lambda)-Bt_2(\lambda)\}\cdot\{k(\lambda)/k_0(\lambda)-1\}$$

$Bt_{O1}(\lambda)$: the corrected total spectral radiant factor of the fluorescent sample;

$Bt_1(\lambda)$: the first total spectral radiant factor of the fluorescent sample;

$Bt_2(\lambda)$: the second total spectral radiant factor of the fluorescent sample;

$k(\lambda)$: a relative ultraviolet(UV) intensity normalized the visible portion of the first measured reference light spectral intensity distribution by an integrated value of a UV portion thereof;

$k_0(\lambda)$: a relative UV intensity normalized the visible portion of the first standard reference light spectral intensity distribution by an integrated value of a UV portion thereof; and the fourth step calculates the total spectral radiant factor of the fluorescent sample by the following equation of $$Bt(\lambda)=\alpha\cdot Bt_{O1}(\lambda)+(1-\alpha)\cdot Bt_2(\lambda)$$

$Bt(\lambda)$: the calculated total spectral radiant factor of the fluorescent sample;

$\alpha$: the weight factor;

$Bt_{O1}(\lambda)$: the corrected total spectral radiant factor of the fluorescent sample;

$Bt_2(\lambda)$: the second total spectral radiant factor of the fluorescent sample.

11. The method in accordance with claim 9, wherein, in the first step, the first and second illumination lights illuminate on the standard fluorescent sample in which a predetermined index calculated from a total spectral radiant factor of that illuminated by an illumination light having a predetermined relative UV intensity is known;

the first standard radiant light spectral intensity distribution of a radiant light radiated from the standard fluorescent sample corresponding to the first illumination light and the second standard radiant light spectral intensity distribution of a radiant light radiated from the standard fluorescent sample corresponding to the second illumination light are alternatively measured; and the first standard reference light spectral intensity distribution of a reference light corresponding to the first illumination light and the second standard reference light spectral intensity distribution of a reference light corresponding to the second illumination light are alternatively measured;

a first total spectral radiant factor of the standard fluorescent sample from the first standard radiant light spectral intensity distribution and the first standard reference light spectral intensity distribution, and a second total spectral radiant factor of the standard fluorescent sample from the second standard radiant light spectral intensity distribution and the second standard reference light spectral intensity distribution are calculated;

a weight factor $A(\lambda)$ with respect to each wavelength is set in a manner to satisfy the following equation;

$$Bt_S(\lambda)=A(\lambda)\cdot Bt_{S1}(\lambda)+\{1-A(\lambda)\}\cdot Bt_{S2}(\lambda)$$

$Bt_S(\lambda)$; the total spectral radiant factor of the standard fluorescent sample;

$A(\lambda)$: the weight factor $\alpha$ set with respect to each wavelength;

$Bt_{S1}(\lambda)$: the first total spectral radiant factor of the standard fluorescent sample;

$Bt_{S2}(\lambda)$: the second total spectral radiant factor of the standard fluorescent sample; and the first standard reference light spectral intensity distribution is memorized into a memory.

12. The method in accordance with claim 9, wherein, in the first step, the first and second illumination lights illuminate on the standard fluorescent sample in which a predetermined index calculated from a total spectral radiant factor of that illuminated by an illumination light having a predetermined relative UV intensity is known;

the first standard radiant light spectral intensity distribution of a radiant light radiated from the standard fluorescent sample corresponding to the first illumination light and the second standard radiant light spectral intensity distribution of a radiant light radiated from the standard fluorescent sample corresponding to the second illumination light are alternatively measured; and the first standard reference light spectral intensity distribution of a reference light corresponding to the first illumination light and the second standard reference light spectral intensity distribution of a reference light corresponding to the second illumination light are alternatively measured;

a first total spectral radiant factor of the standard fluorescent sample from the first standard radiant light spectral intensity distribution and the first standard reference light spectral intensity distribution, and a second total spectral radiant factor of the standard fluorescent sample from the second standard radiant light spectral intensity distribution and the second standard reference light spectral intensity distribution are calculated;

the weight factor $\alpha$ with respect to each wavelength is set in a manner to satisfy the following equation;

$$Bt_S(\lambda) = \alpha \cdot Bt_{S1}(\lambda) + (1-\alpha) \cdot Bt_{S2}(\lambda)$$

$Bt_S(\lambda)$; the total spectral radiant factor of the standard fluorescent sample;
$\alpha$: the weight factor;
$Bt_{S1}(\lambda)$: the first total spectral radiant factor of the standard fluorescent sample;
$Bt_{S2}(\lambda)$: the second total spectral radiant factor of the standard fluorescent sample; and the first standard reference light spectral intensity distribution is memorized into the memory.

13. The method in accordance with claim 9, wherein the cutoff frequency is the shortest wavelength of the visible light.

14. The method in accordance with claim 9 further comprising a fifth step for calculating an index with respect to a color from the total spectral radiant factor.

15. An apparatus for measuring a spectral property of a fluorescent sample comprising:

a first spectroscope for measuring a spectral intensity distribution of a radiant light radiated from a sample;

a second spectroscope for measuring a spectral intensity distribution of a reference light which is similar to an illumination light;

a factor processor for calculating a weight factor from a standard radiant light spectral intensity distribution measured by the first spectroscope and a standard reference light spectral intensity distribution measured by the second spectroscope when a predetermined sample disposed at a measurement position illuminated by an illumination light;

a memory for memorizing the weight factor;

a first processor for calculating a spectral radiant factor of a fluorescent sample to be measured from a measured radiant light spectral intensity distribution measured by the first spectroscope, a measured reference light spectral intensity distribution measured by the second spectroscope and the weight factor; and a second processor for correcting the spectral radiant intensity by using a first ratio of a visible portion of the standard reference light spectral intensity distribution against a ultraviolet portion thereof, and a second ratio of a visible portion of the measured reference light spectral intensity distribution against a ultraviolet portion thereof.

* * * * *